United States Patent [19]
Wuonola et al.

[11] Patent Number: 6,090,953
[45] Date of Patent: Jul. 18, 2000

[54] PYRONIN ANTIBACTERIALS, PROCESS AND NOVEL INTERMEDIATES THERETO

[75] Inventors: Mark A. Wuonola, Waltham; Gary R. Gustafson, Bedford; James S. Panek, Randolph; Tao Hu; Jennifer V. Schaus, both of Boston, all of Mass.

[73] Assignees: Scriptgen Pharmaceuticals, Inc., Boston; Trustees of Boston University, Waltham, both of Mass.

[21] Appl. No.: 09/370,533

[22] Filed: Aug. 9, 1999

Related U.S. Application Data

[62] Division of application No. 08/822,323, Mar. 21, 1997.
[60] Provisional application No. 60/013,874, Mar. 22, 1996.

[51] Int. Cl.$^7$ .................................................. C07D 309/32
[52] U.S. Cl. .................................................. 549/291
[58] Field of Search .............................................. 549/291

[56] References Cited

PUBLICATIONS

Hu, T. et al., *J. Org. Chem.* 63:2402–2403, 1998.
Jansen et al., Chemical Abstract, 103:3291, 1985.
Jarolim et al., Chemical Abstract, 85:123296, 1976.
Kohl et al., *Leibigs Ann. Chem.* 6:1088–93, 1984, (Abstract).
Sharma et al., Chemical Abstract, 99:38646, 1982.

*Primary Examiner*—Johann Richter
*Assistant Examiner*—Taofiq A. Solola
*Attorney, Agent, or Firm*—Darby & Darby

[57] ABSTRACT

The present invention provides convergent processes for preparing myxopyronins and corallopyronins, compounds useful as antibacterial therapeutics. The present invention also provides novel compositions of matter which are useful for the preparation of pyronin antibiotics.

8 Claims, 20 Drawing Sheets

PYRONIN ANTIBACTERIALS, PROCESS AND NOVEL INTERMEDIATES THERETO

This application is a division of Ser. No. 08/822,323 filed Mar. 21, 1997 which is based on U.S. Provisional Application Ser. No. 60/013,874, filed Mar. 22, 1996, the contents of which are hereby incorporated by reference into this application.

FIELD OF THE INVENTION

The present invention is in the field of pyronin antibiotics. In particular, the present invention relates to processes for the preparation of myxopyronins and corallopyronins, compounds useful as antibacterial therapeutics. The present invention also provides novel compositions of matter which are useful as intermediates for preparing the pyronin antibiotics.

Throughout this application, various publications are referred to, each of which is hereby incorporated by reference in its entirety into this application to more fully describe the state of the art to which the invention pertains.

BACKGROUND OF THE INVENTION

Myxopyronins and corallopyronins are 2-pyrone-containing antibiotics which present a significant opportunity in antibacterial therapy. They constitute a synthetically accessible, unexploited series of low molecular weight bacterial RNA polymerase (RNAP) inhibitors with favorable properties: selectivity vs. human RNAP, cell penetration (minimal inhibitory concentrations (MICs) at concentrations comparable to in vitro bacterial RNAP $IC_{50}$s), and potency against rifampicin-resistant *S. aureus* equal to that against a rifampicin-susceptible strain.

Corallopyronin A/B and myxopyronin A/B are natural products isolated from gliding bacteria (*Corallococcus coralloides; Myxococcus fulvus*) and discovered to be RNAP inhibitors. Reichenbach, H., Höfle, G., Irschik, H., Kohl, W., *Liebigs Ann. Chem.*, 1983, 1656; Reichenbach, H., Höfle, G., Irschik, H., Kohl, W., *Liebigs Ann. Chem.*, 1984, 1088; Reichenbach, H., Höfle, G., Irschik, H., Jansen, R., *Liebigs Ann. Chem.*, 1985, 822. The structures of these compounds are closely related having in common a 3-acyl-4-hydroxy-2-pyrone with an alkyl chain at the 6-position bearing a vinyl carbamate functionality, a feature atypical of natural products. They differ only in the substitution on the alkyl chain attached to the 3-position of the pyrone, the corallopyronins being more elaborate (FIG. 1(*a*)). The pyronins have good intrinsic activity in antibacterial assays against both *E. coli* and *S. aureus* RNA polymerase. This activity is specific with respect to human or SP6 polymerases. MIC data (see Table I) show that these compounds, like rifampicin, are not absorbed well by *E. coli* but that they have intrinsic activity against both gram positive and gram negative bacteria.

An attractive feature of this series of compounds is their activity against strains resistant to rifampicin. The MIC for rifampicin is ca. 10 nM against susceptible strains, but falls off against resistant strains (MIC>10 $\mu$M). The use of rifampicin is limited by the development of bacterial resistance. Both myxo- and corallopyronins are equiactive against Rif-susceptible and Rif-resistant *S. aureus*.

Pyrones have been used in the prior art to elicit a biological effect in a few instances, but in none of these instances have they been used as an antibacterial agent. 2H-Pyran-2,6(3H)-dione derivatives are reported to be active at reasonable doses in a passive cutaneous anaphylaxis model in rats when administered by either the intravenous or oral route. Snader, K. M. et al., *J. Med. Chem.*, 1979, 22, 706; Chahrin, L. W., Snader, K. M., Williams, C. R., 2H-Pyran-2,6(3H)-dionederivate. German Patent 25 33 843. In a second case, simple 3-(1-oxoalkyl)-4-hydroxy-6-alkyl-2-pyrones were found to be effective in vitro in the inhibition of human sputum elastase. Cook, L., Ternai, B., Ghosh, P., *J. Med. Chem.*, 1987, 30, 1017. Lastly, a series of pyrone derivatives were found to be effective inhibitors of HIV protease in both enzymatic assays and cell culture (FIG. 1(*b*)). Skulnick, H. I., et al., *J. Med. Chem.*, 1995, 38, 4968. No synthetic investigations or medicinal uses of pyronin antibacterials have been reported in the literature.

The present invention provides novel intermediates useful in the synthesis of myxopyronin A and derivatives thereof. In addition, the present invention provides processes for synthesizing myxopyronin A and derivatives thereof as well as corallopyronins.

SUMMARY OF THE INVENTION

One object of the present invention is to provide processes for the preparation of myxopyronins and corallopyronins, compounds useful as antibacterial therapeutics.

Another object of the present invention is to provide various compositions of matter useful as intermediates in the preparation of the antibiotic myxopyronin.

A further object of the present invention is to provide methods of preparing such intermediates.

BRIEF DESCRIPTION OF THE DRAWINGS

FIG. 1(*b*) illustrates coumarin derivatives which inhibit HIV protease in enzymatic assays and cell culture. Skulnick, H. I., et al., *J. Med. Chem.*, 1995, 38, 4968.

TABLE I

| | In Vitro $IC_{50}$ ($\mu$M) | | | | | MIC ($\mu$g/ml) | | |
|---|---|---|---|---|---|---|---|---|
| Compound | E. coli RNAP | S. aureus RNAP | Human RNAP | SP6 RNAP | Rev/RRE | S. aureus | E. coli MCR | E. coli BAS |
| Myxopyronin A/B | 10 | 10 | >200 | >200 | 100 | 4 | 180 | 1.6 |
| Corallopyronin A/B | 6 | 10 | >200 | >200 | 100 | 4 | >200 | 0.4 |

Figure 6A:
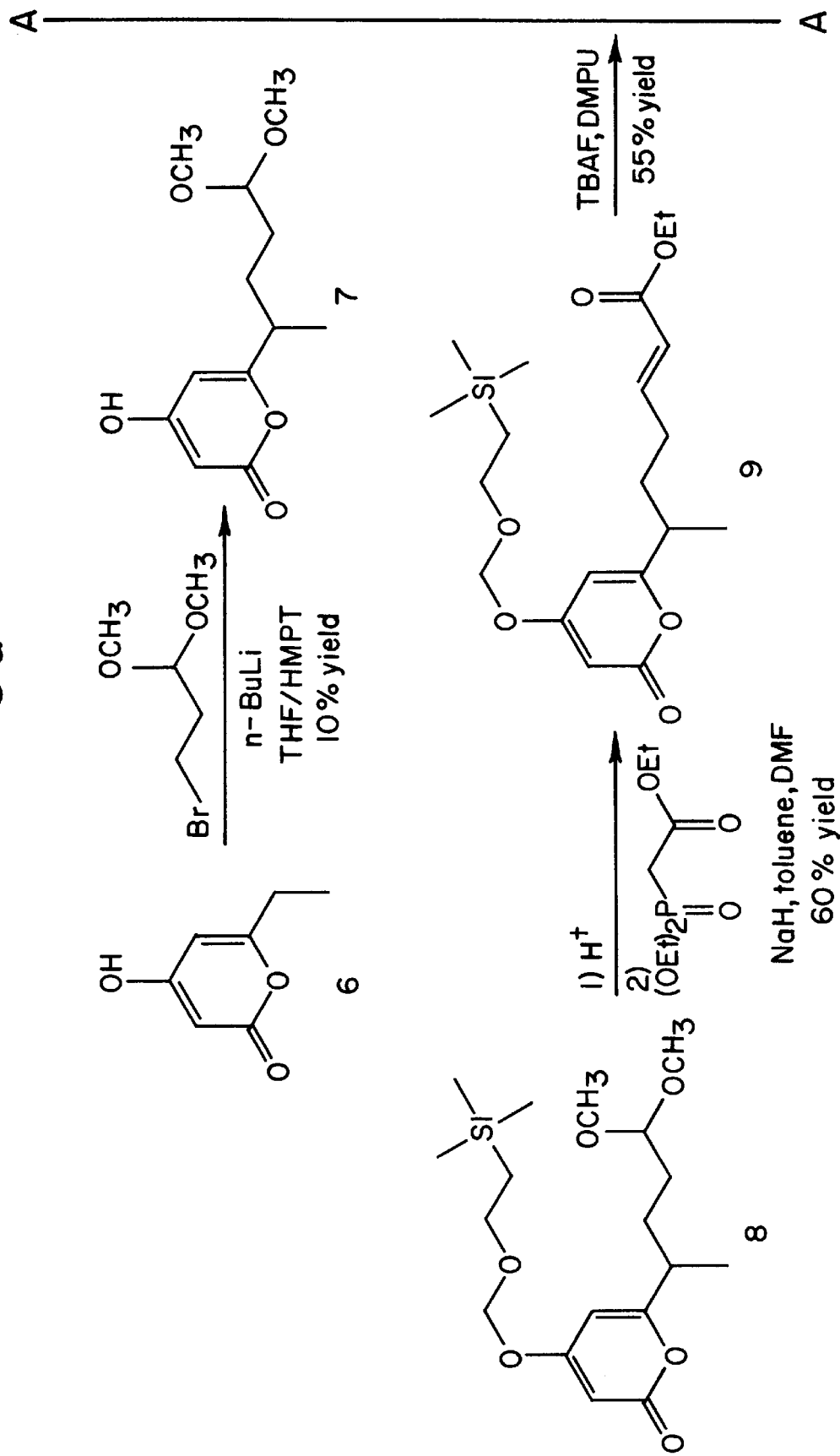
Figure 6B:
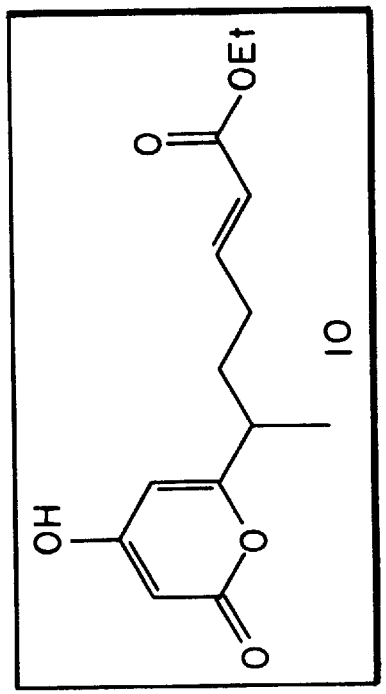

FIGS. 6A and 6B illustrates the synthesis of compound 10 in accord with the present invention.

Figure 7:
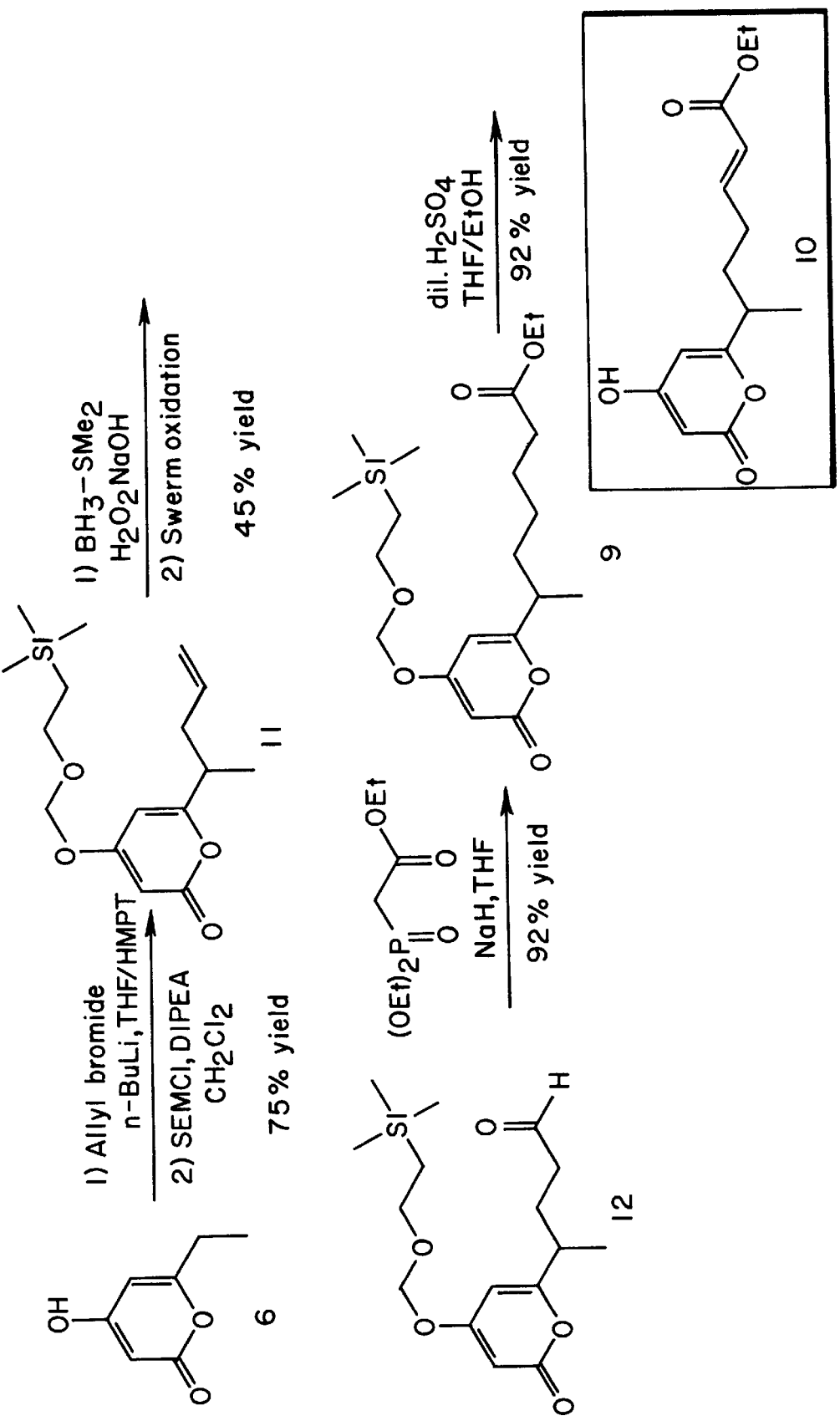

FIG. 7 illustrates an alternative synthesis of compound 10 in accord with the present invention.

Figure 8A:
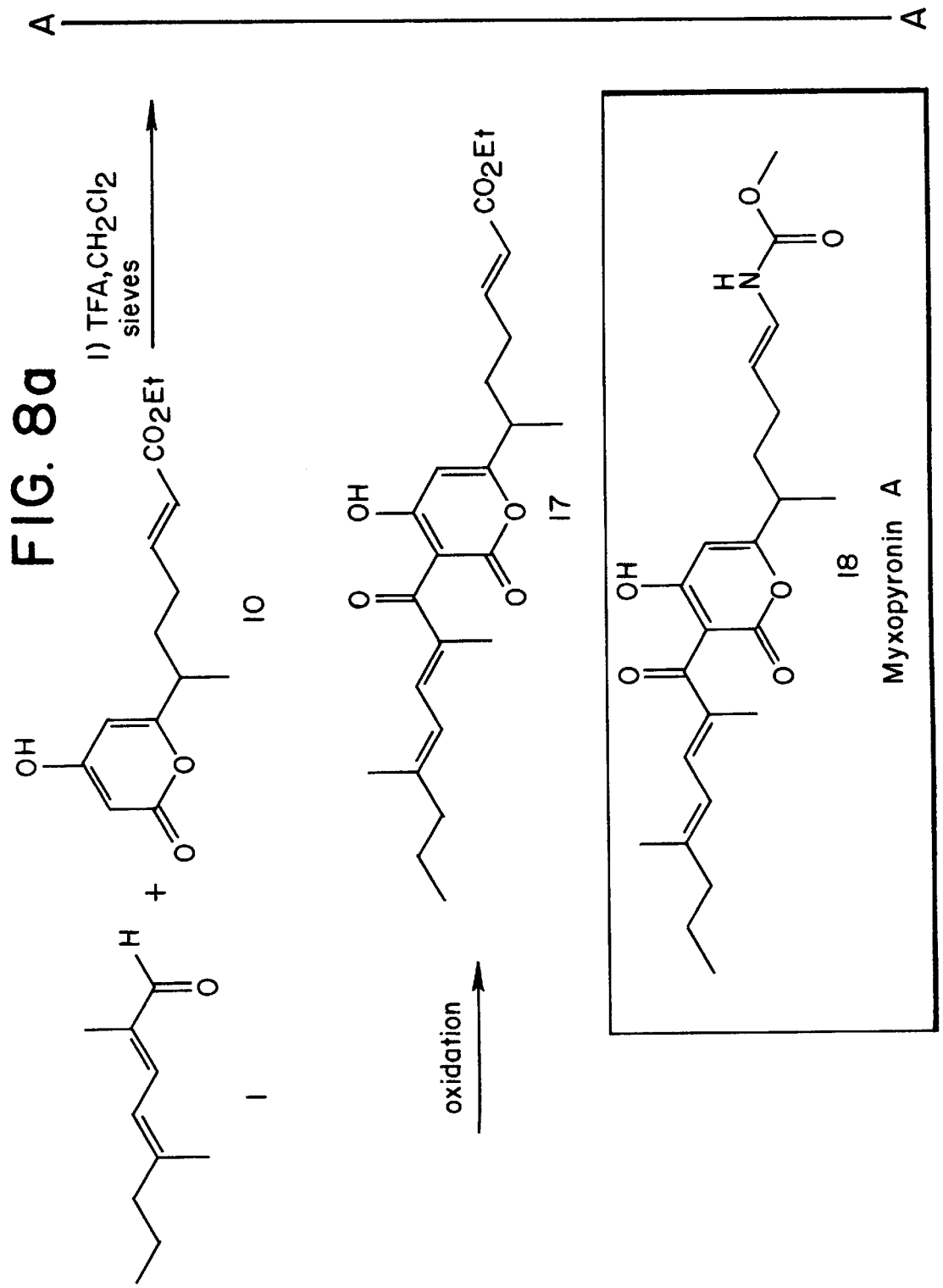
Figure 8B:
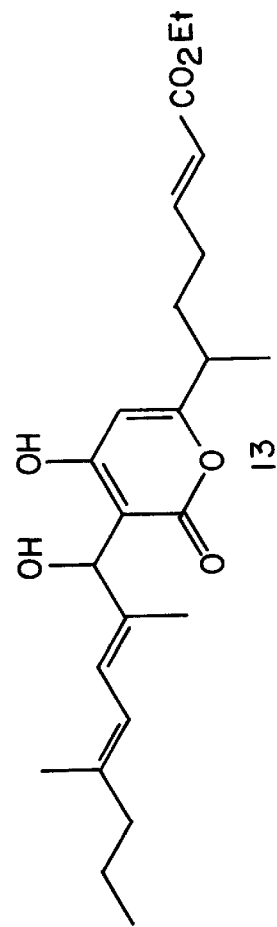

FIGS. 8A and 8B illustrates the synthesis of compound 18 in accord with the present invention.

Figure 9:
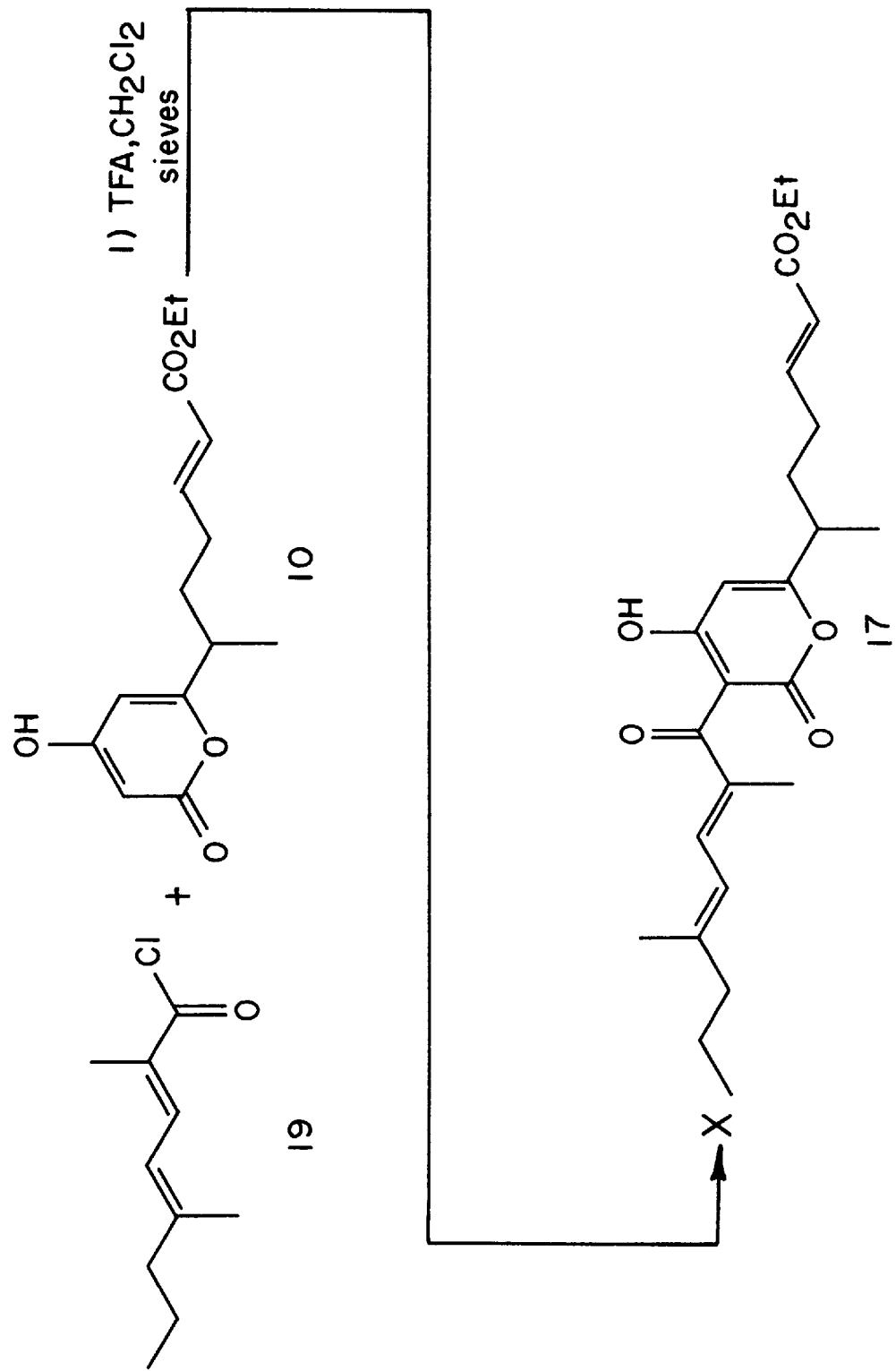

FIG. 9 illustrates the attempted acylation of pyrone 10 with acyl chloride 19.

Figure 10A:
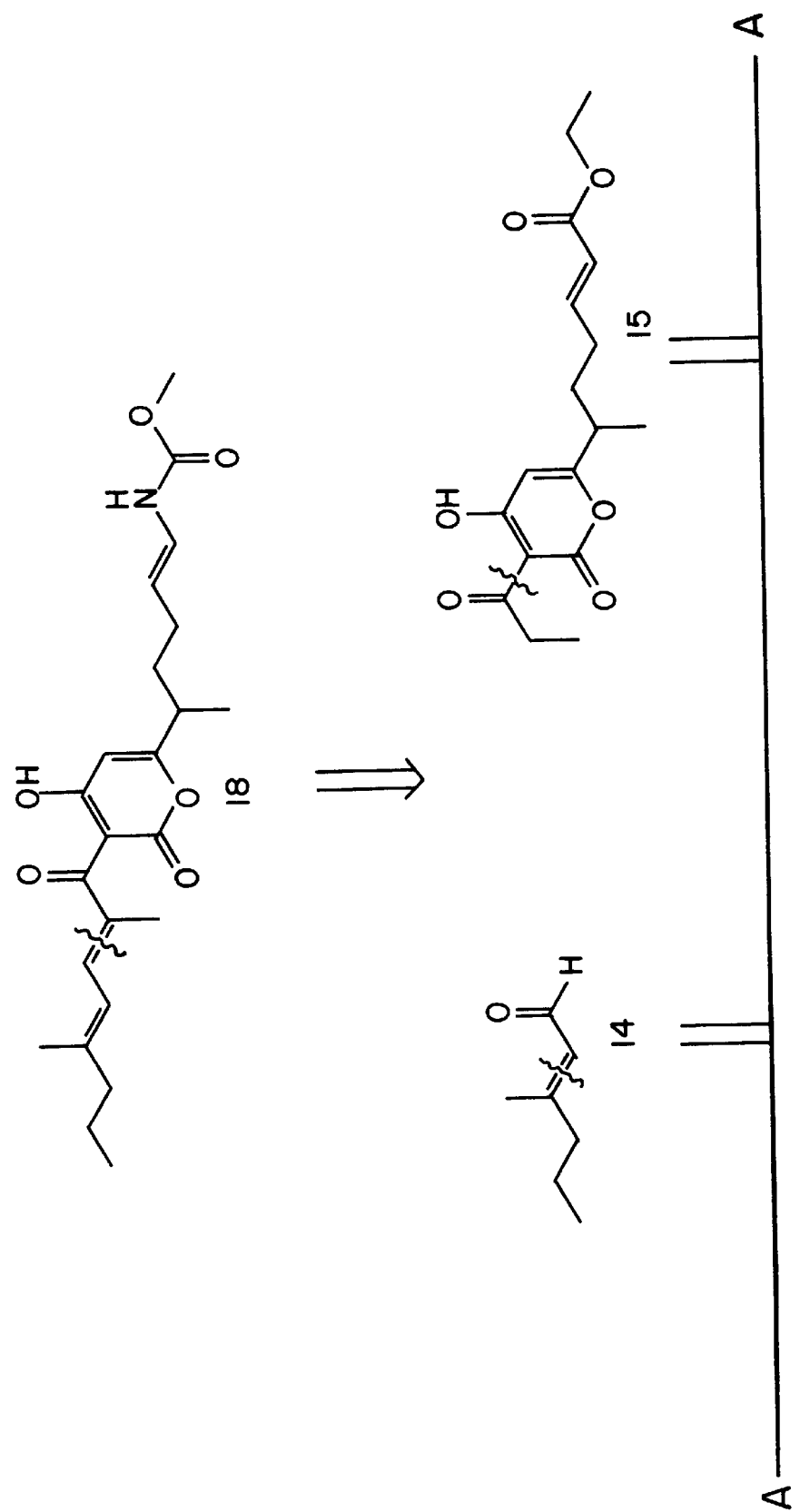
Figure 10B:
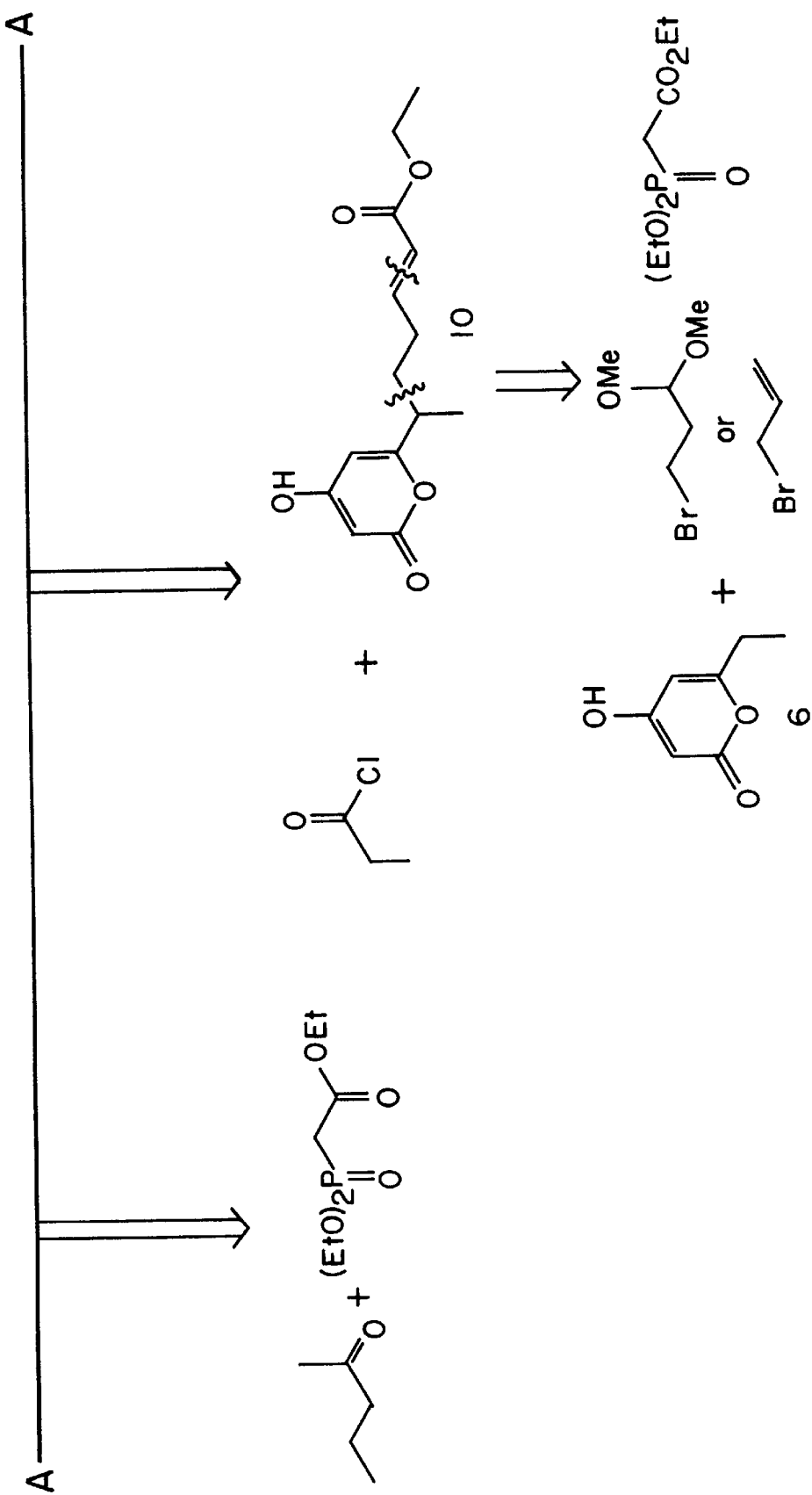

FIGS. 10A and 10B illustrates an alternative retrosynthetic analysis for the preparation of myxopyronin A.

Figure 11A:
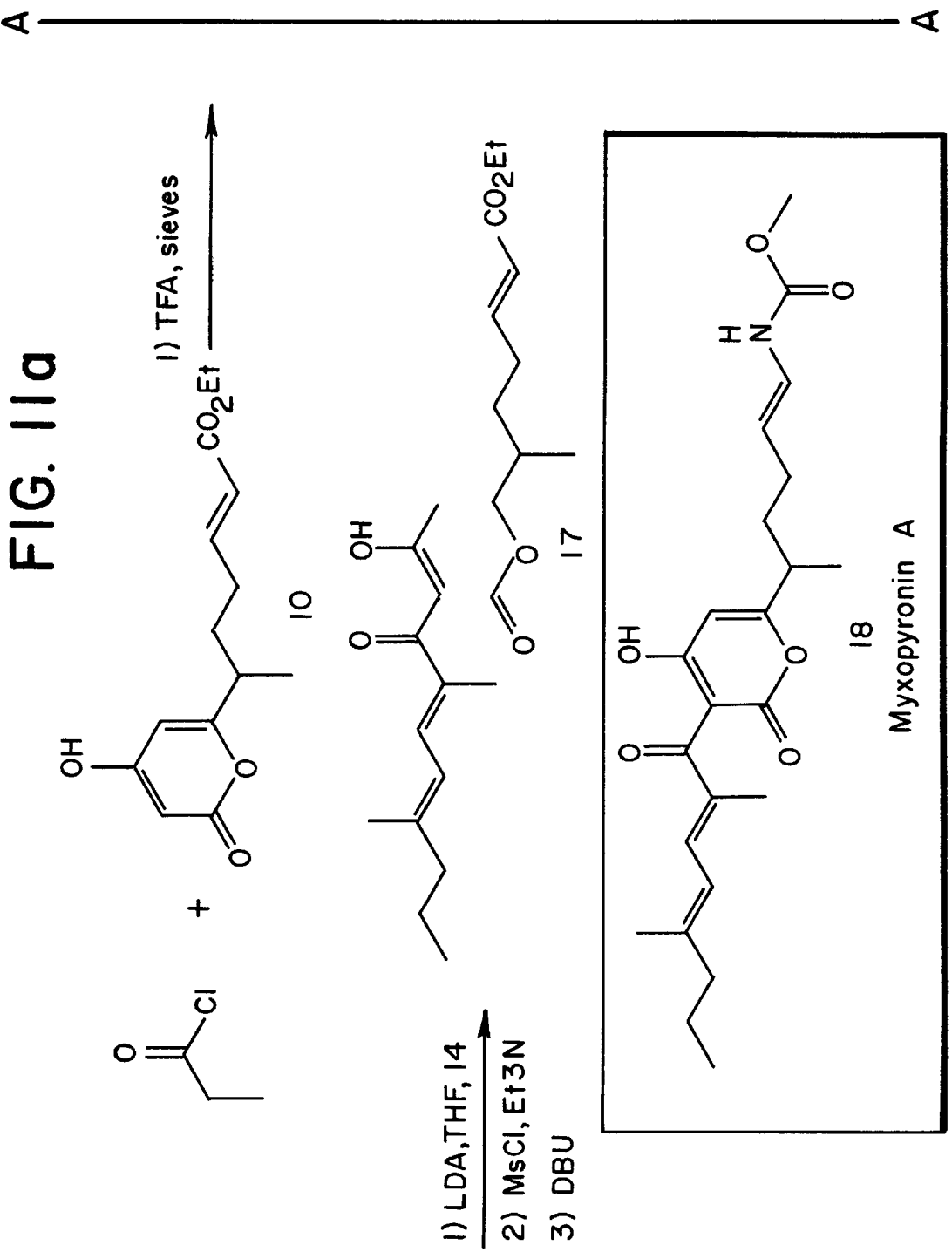
Figure 11B:
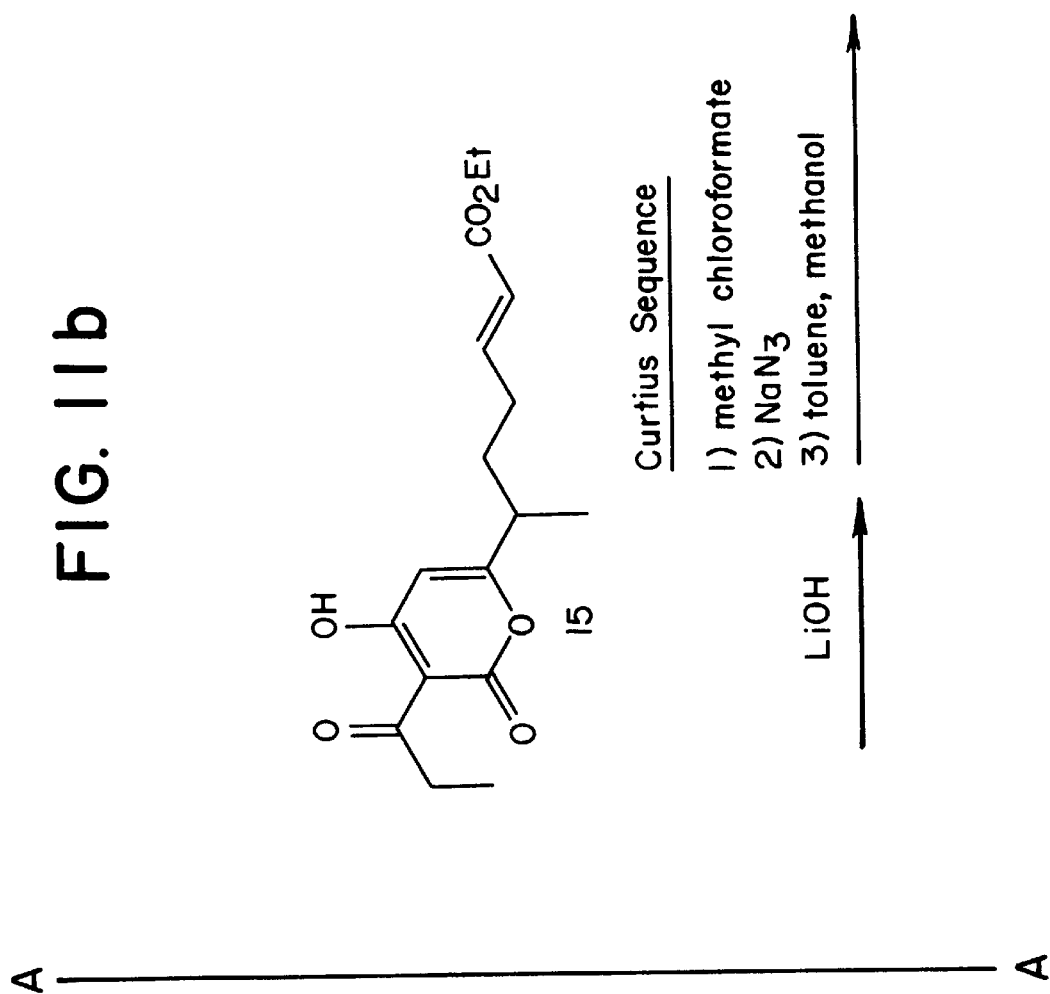

FIGS. 11A and 11b illustrates the synthesis of compound 18 in accord with the present invention.

Figure 12:
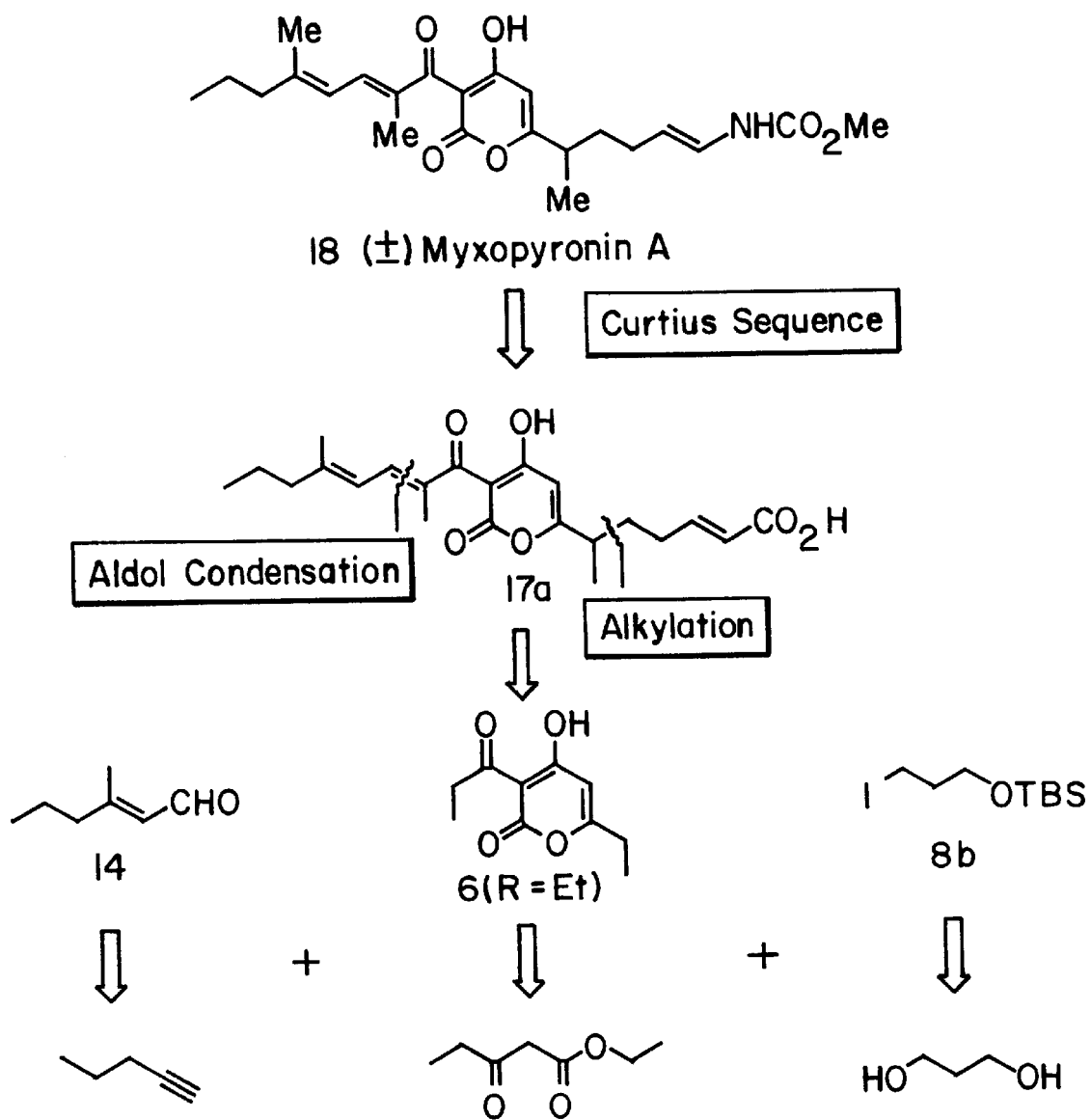

FIG. 12 shows a retrosynthetic analysis of myxopyronin A.

Figure 12A:
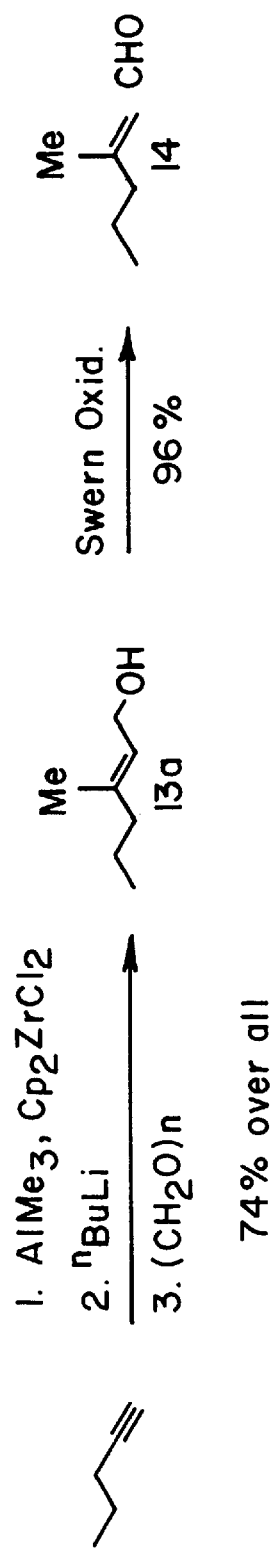

FIG. 12(a) shows the preparation of allyl aldehyde 14.

Figure 12B:
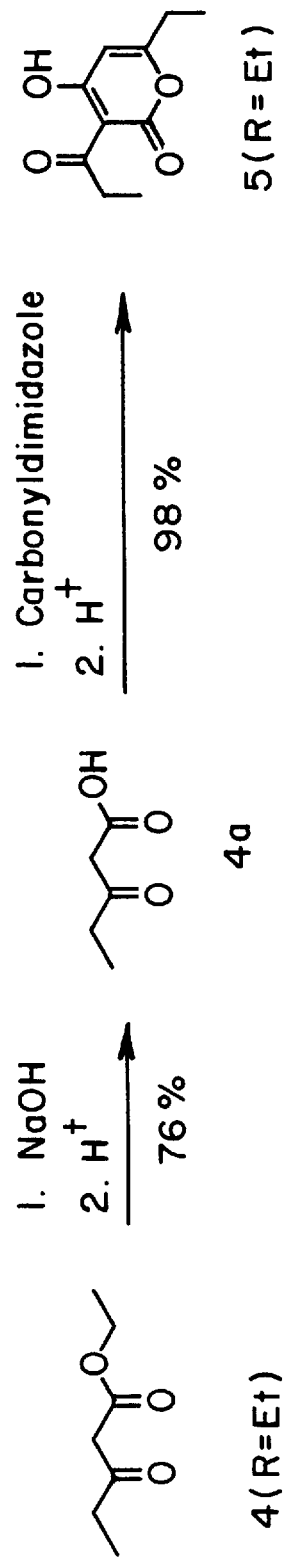

FIG. 12(b) shows the preparation of acylated pyrone 5.

Figure 12C:
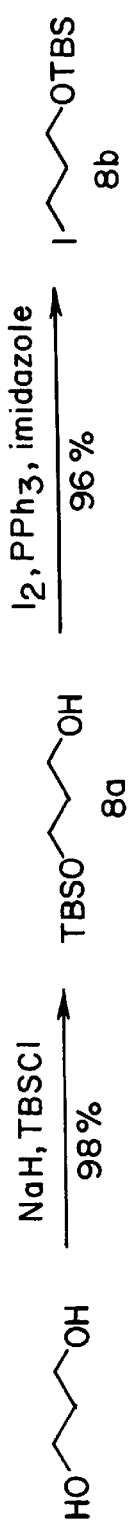

FIG. 12(c) shows the preparation of iodide 8b.

Figure 13A:
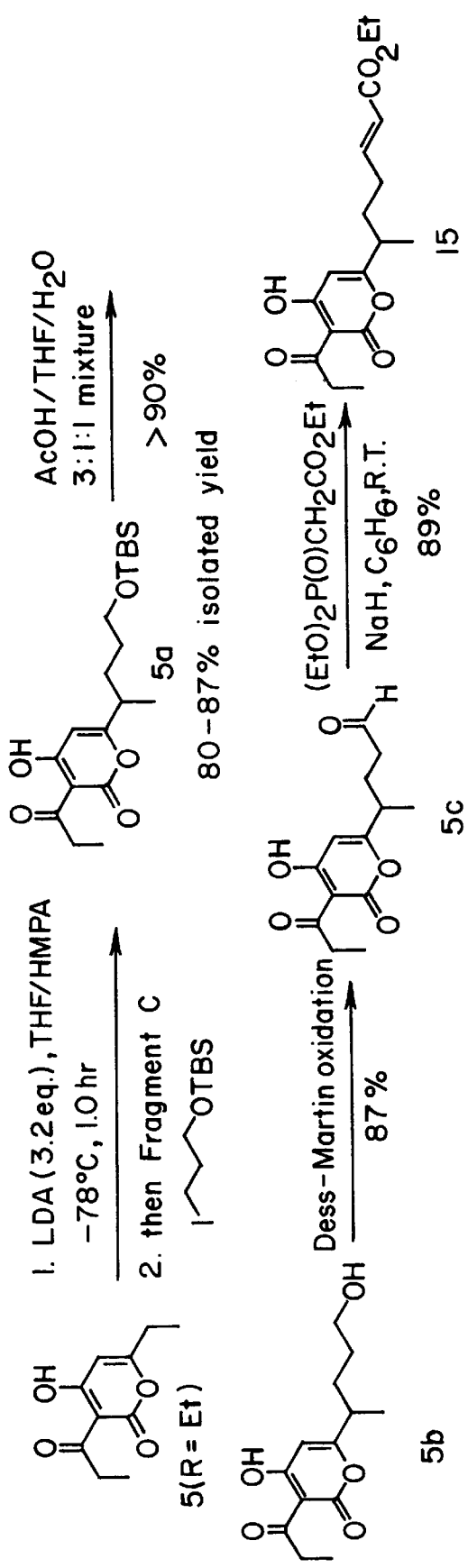

FIG. 13(a) provides a synthetic route to acyl pyrone intermediate 15.

Figure 13B:
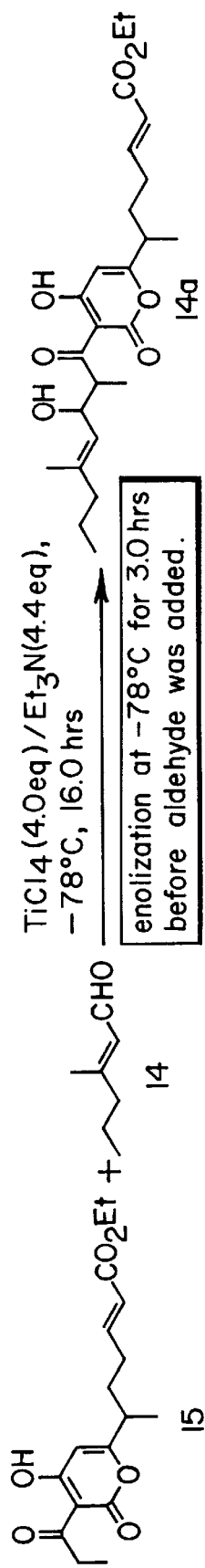

FIG. 13(b) illustrates the condensation reaction of intermedites 14 and 15 and subsequent elaboration to myxopyronin A.

Figure 14A:
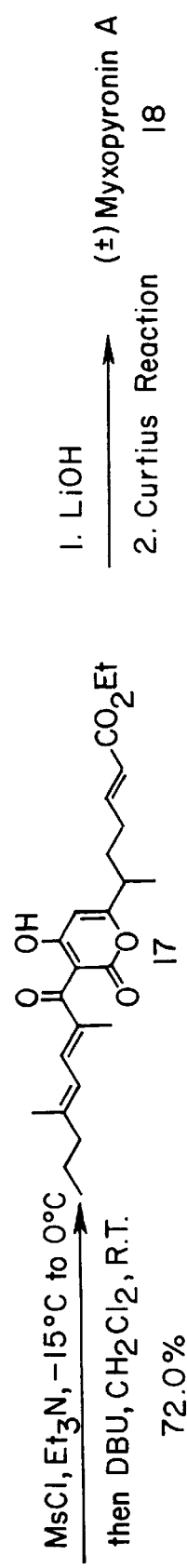

FIG. 14(a) shows the preparation of allyl aldehyde 14.

Figure 14B:
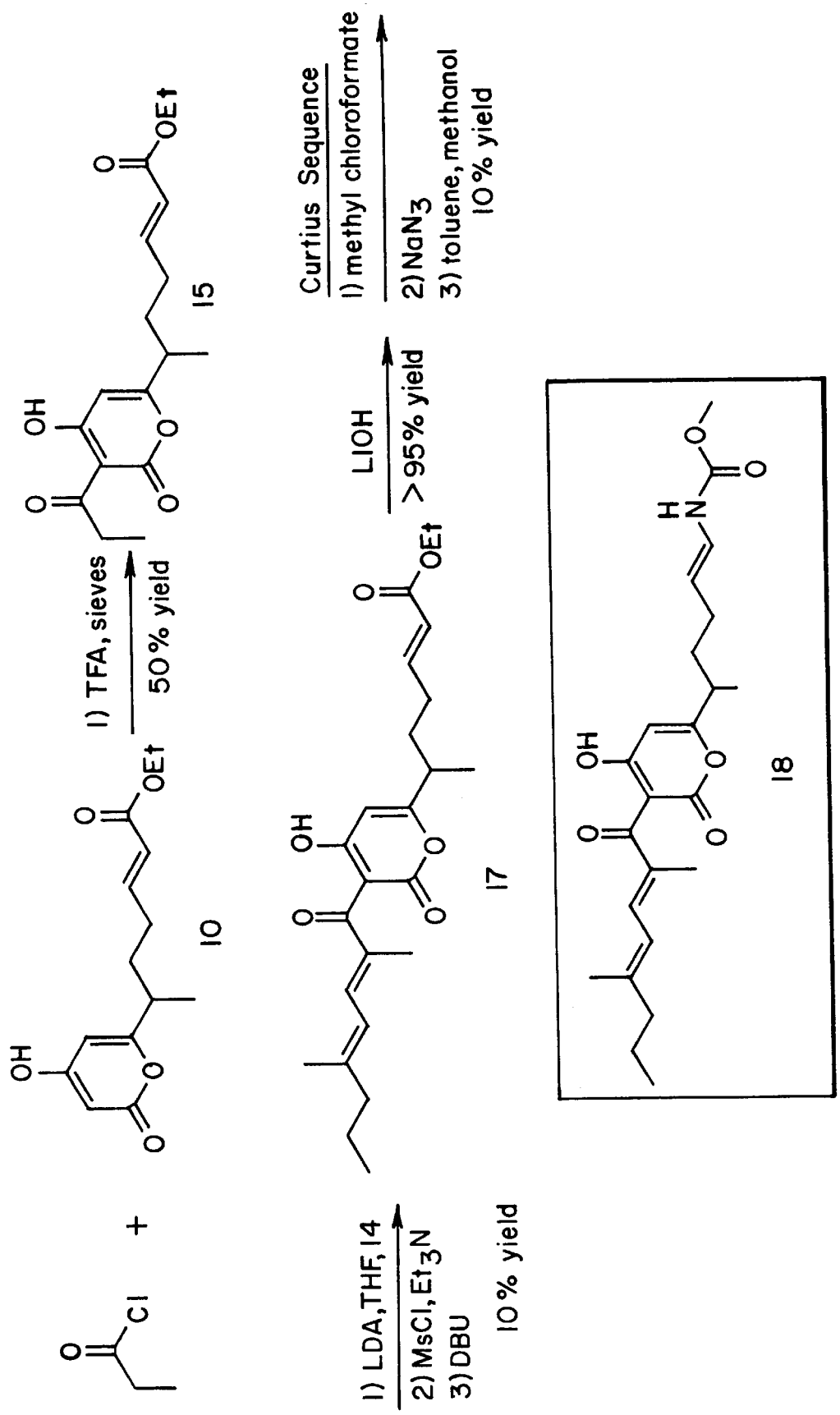

FIG. 14(b) shows the acylation of pyrone 10 with propionyl chloride and subsequent elaboration to myxopyronin A.

Figure 15:
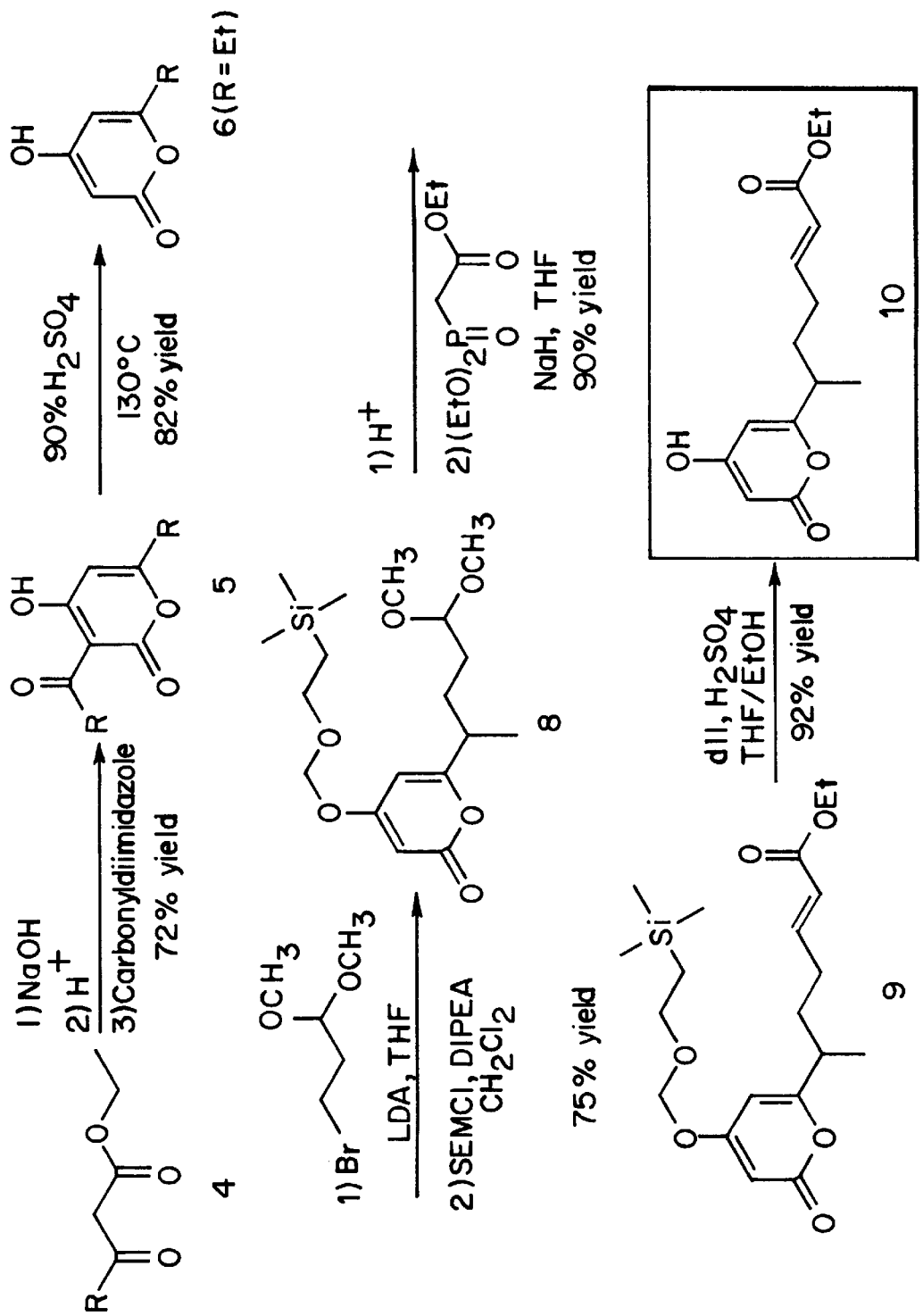

FIG. 15 provides a synthetic route to intermediate pyrone 10.

DETAILED DESCRIPTION OF THE INVENTION

The present invention provides a convergent synthetic route to prepare myxopyronin compounds. The invention provides two variant pathways based on alternative approaches to install the side chain at the pyrone 3-position.

Pathway A

Starting with 2-pentanone, a Wadsworth-Emmons reaction is performed with triethyl phosphonoacetate in THF in the presence of NaH. Ester 16 (see FIG. 3) is sequentially reduced with DIBAL and oxidized with DDQ to produce aldehyde 14. A Wadsworth-Emmons reaction is used to condense aldehyde 14 and triethyl 2-phosphonopropionate in THF in the presence of NaH. The resulting product is sequentially reduced with DIBAL and oxidized with DDQ to produce aldehyde 1. This constitutes the 3-position side chain precursor.

The pyrone portion is constructed as follows. Ethyl propionylacetate is hydrolyzed with aqueous NaOH. Two equivalents of the resulting acid are condensed with an equivalent of carbonyldiimidazole to produce pyrone 5 (see FIG. 5). The 3-propionyl group is hydrolyzed using concentrated $H_2SO_4$ at elevated temperature to afford pyrone 6, which is then alkylated with 3-bromopropionaldehyde dimethylacetal using n-BuLi and THF/HMPT as a solvent to give 7. The 4-position hydroxyl is converted to SEM ether 8 using SEM-Cl and diisopropylamine in $CH_2Cl_2$. The dimethylacetal is removed under acidic conditions and the resulting aldehyde is alkylated under Wadsworth-Emmons conditions with triethylphosphonoacetate in THF in the presence of NaH to produce the unsaturated ester 9. The SEM ether is cleaved using TBAF and DMPU to give key intermediate 10.

Intermediate 10 can be synthesized by an alternate pathway. Pyrone 6 is deprotonated with n-BuLi and then alkylated with allyl bromide in THF/HMPT. The 4-position hydroxyl is converted to SEM ether 11 by treatment with SEM-Cl and diisopropylamine in $CH_2Cl_2$. The allyl group is hydroborated using a borane reagent and the subsequent borate is removed oxidatively to give the alcohol. The resulting alcohol is oxidized under standard Swern conditions to give aldehyde 12. Aldehyde 12 was alkylated with triethylphosphonoacetate in THF in the presence of NaH to produce unsaturated ester 9. The SEM ether is removed under acidic conditions, e.g., using $H_2SO_4$ in THF/EtOH, to give the key intermediate 10. An aldol reaction between compounds 1 and 10 catalyzed by TFA in $CH_2Cl_2$ provides intermediate 13. The synthesis can be finished by oxidation to produce intermediate 17 followed by a Curtius sequence to produce myxopyronin A 18.

Pathway B

The second route takes advantage of the convenient availability of intermediates 10 and 14 by processes disclosed below. Pyrone 10 is acylated with propionyl chloride in TFA at elevated temperature to afford intermediate 15 (FIG. 11). A base-catalyzed aldol between compounds 14 and 15 using LDA in THF forms an intermediate that is sequentially treated with mesyl chloride and triethylamine in $CH_2Cl_2$ followed by DBU to afford compound 17, which is also an intermediate in pathway A. Myxopyronin A results after a Curtius sequence.

The present invention provides a process of preparing a myxopyronin having the structure:

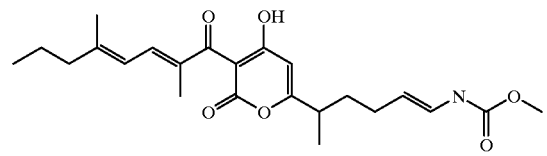

which comprises:

(a) condensing an aldehyde having the structure:

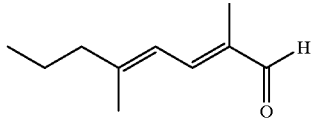

with a pyrone having the structure:

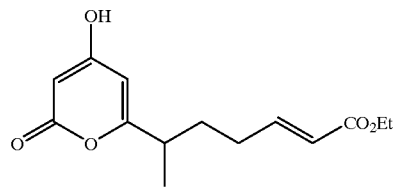

under suitable conditions to form an adduct having the structure:

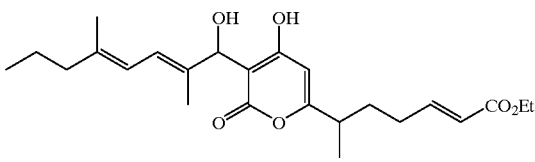

(b) oxidizing the adduct formed in step (a) under suitable conditions to form a pyrone ketone having the structure:

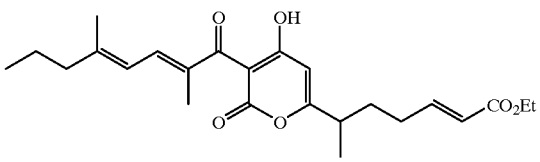

and (c) (i) saponifying the pyrone ketone formed in step (b) under suitable conditions to form a pyrone acid;
(ii) acylating the pyrone acid formed in step (c) (i) under suitable conditions to form a pyrone anhydride; and
(iii) treating the pyrone anhydride formed in step (c) (ii) with an azide salt to form a pyrone acyl azide; and
(iv) heating the pyrone acyl azide formed in step (c) (iii) in methanol under suitable conditions to form myxopyronin A.

As practiced in the present invention, the 1,2-addition step (a) recited above is performed using an acid catalyst, such as trifluoroacetic acid (TFA), hydrochloric acid, sulfuric acid, or p-toluenesulfonic acid, preferably in the presence of a dehydrating agent, such as molecular sieves, more preferably using 4 Å molecular sieves, in an inert organic solvent, such as dichloromethane or p-dioxane. Alcohol oxidation step (b) is carried out using various oxidants, such as 2,3-dichloro-5,6-dicyano-1,4-benzoquinone (DDQ), manganese dioxide or chromium chlorochromate. Saponifying step (c) (i) is carried out using a hydroxide base, such as LiOH, NaOH, KOH or CsOH, in a solvent mixture comprising water and at least one organic co-solvent, such as methanol, ethanol, or tetrahydrofuran (THF). A preferred solvent composition is methanol/THF/water in the proportion 2:2:1. In the Curtius sequence, step (c) (ii) is effected using an alkyl or aryl chloroformate, including, but not limited to, methyl chloroformate, ethyl chloroformate, isopropyl and phenyl chloroformate, in the presence of a base, such as DIPEA, in an inert organic solvent, preferably miscible with water, preferably, acetone. The resulting product may be purified, or used directly in the subsequent step. Step (c) (iii) is carried out using an azide salt, such as lithium azide, sodium azide, or tetraalkylammonium azide, preferably in the presence of water. Rearrangement step (c) (iv) entails heating the acid azide formed in step (c) (iii) in a solvent mixture, containing an alcohol, such as ethanol, methanol, or phenol, preferably, methanol, and an inert solvent such as benzene or toluene, at elevated temperatures, preferably, at the reflux temperature of the solvent mixture.

The present invention also provides a process of preparing a myxopyronin having the structure:

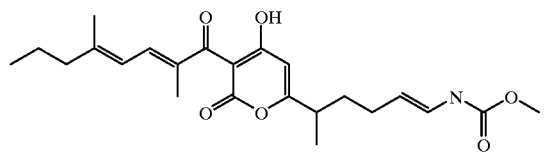

which comprises:
(a) treating a pyrone having the structure:

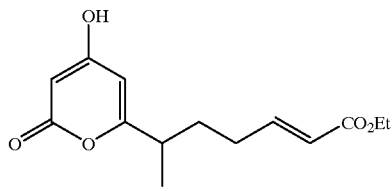

with propionyl chloride under suitable conditions to form a ketone adduct having the structure:

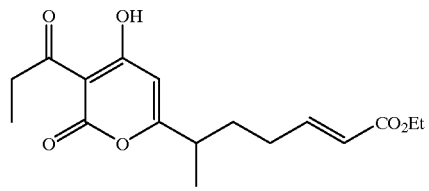

(b) (i) condensing the ketone adduct formed in step (a) under suitable conditions with an aldehyde having the structure:

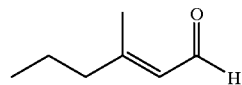

to form a pyrone aldol; (ii) mesylating the pyrone aldol formed in step (b) (i) under suitable conditions to form a pyrone aldol mesylate; and (iii) reacting the pyrone aldol mesylate under suitable basic conditions to form a pyrone ketone having the structure:

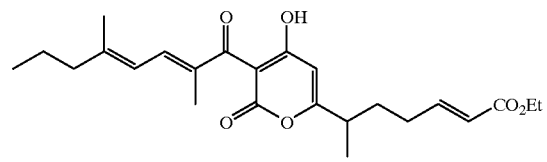

and (c) (i) saponifying the pyrone ketone formed in step (b) (iii) under suitable conditions to form a pyrone acid;
(ii) acylating the pyrone acid formed in step (c) (i) under suitable conditions to form a pyrone anhydride; and
(iii) treating the pyrone anhydride formed in step (c) (ii) with an azide salt to form a pyrone acyl azide, and (iv) heating the pyrone acyl azide formed in step (c) (iii) under suitable conditions to form the myxopyronin.

Acylation step (a) may be effected using an acid catalyst, such as TFA, hydrochloric acid, or p-toluenesulfonic acid, preferably in the presence of a dehydrating agent, such as molecular sieves, preferably using 4 Å molecular sieves, in an inert organic solvent, such as dichloromethane. Condensation step (b) (i) is performed using a strong, non-nucleophilic base, such as LDA, potassium t-butoxide, or sodium hydride, preferably, LDA, in an inert organic solvent, such as THF. Mesylation step (b) (ii) is carried out using an acylating agent, such as mesyl chloride, p-tosyl chloride, acetic anhydride, preferably, mesyl chloride, in the presence of a non-nucleophilic organic base, such as DIPEA or triethylamine. Elimination step (b) (iii) may be performed using a variety of reagents effective to cause elimination, preferably, a strong non-nucleophilic base such as DBU. The Curtius rearrangment is effected as described above.

The present invention also provides a process of preparing an unsaturated aldehyde having the structure:

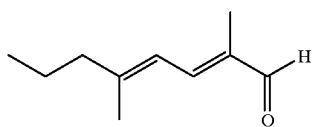

which comprises:

(a) condensing triethyl phosphonoacetate with 2-pentanone under suitable conditions to form an unsaturated ester having the structure:

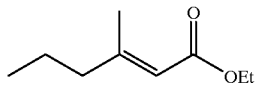

(b) (i) reducing the unsaturated ester formed in step (a) under suitable conditions to form an unsaturated alcohol; and (ii) oxidizing the unsaturated alcohol under conditions suitable to form a monounsaturated aldehyde having the structure:

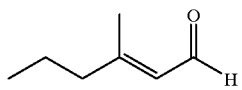

and (c) (i) condensing triethyl phosphonopropionate with the monounsaturated aldehyde formed in step (b) (ii) under suitable conditions to form a diene ester;
(ii) reducing the diene ester formed in step (c) (i) under suitable conditions to form a diene alcohol; and
(iii) oxidizing the unsaturated alcohol under suitable to form the unsaturated aldehyde.

As implemented in the present invention, the condensation step, preferably of the Wadsworth-Emmons type, is favorably performed in the presence of a non-nucleophilic base, such as LDA or sodium hydride, in an inert polar, aprotic organic solvent, such as THF. The ester reduction step (b) (i) may be carried out using any of a variety of reducing agents, such as diisobutylaluminum hydride (DIBAL) in an inert aprotic organic solvent, such as THF. Oxidation step (b) (ii) may be effected using any of a range of mild oxidants, preferably, DDQ, in an inert organic solvent, such as dichloromethane. The subsequent condensation step (c) (i) may be performed in the presence of a non-nucleophilic base, such as sodium hydride, in an inert organic solvent, preferably, THF. Reduction step (c) (ii) may be carried out using various reducing agents, preferably, diisobutyl-aluminum hydride (DIBAL) in an aprotic organic solvent, such as THF. Finally, oxidation step (c) (iii) may be effected using a variety of oxidants, such as DDQ, in dichloromethane.

In one embodiment, the present invention provides a process of preparing the unsaturated ester having the structure:

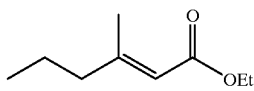

which comprises (a) condensing ethyl butyryl acetate with diethyl phosphorochloridate under suitable conditions to form an enol phosphonate; and (b) alkylating the enol phosphonate formed in step (a) with an organometallic reagent under suitable conditions to form the unsaturated ester.

As practiced in the invention, condensing step (a) is performed using a non-nucleophilic base, including, but not limited to, potassium t-butoxide, sodium hydride, LDA, and lithium diethylamide, preferably, sodium hydride, in an inert aprotic organic solvent, such as THF or diethyl ether. Alkylation step (b) is effected using an organometallic reagent, such as lithium dimethyl cuprate, methyl lithium, methyl magnesium bromide or chloride, preferably, lithium dimethyl cuprate, in an inert aprotic solvent, preferably, diethyl ether, at a temperature ranging from about −100° C. to about 0° C., more preferably, from about −90° C. to about −50° C., most preferably, at −78° C.

In addition, the present invention provides a process of preparing a pyrone ester having the structure:

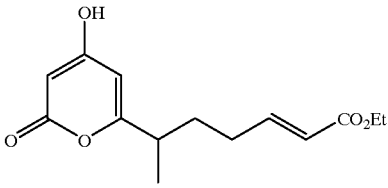

which comprises:
(a) treating a dicarbonyl compound having the structure:

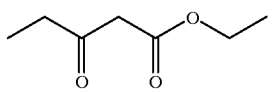

acidifying and dimerizing under suitable conditions to form an acyl pyrone having the structure:

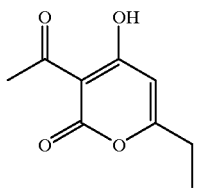

(b) hydrolyzing the acyl pyrone formed in step (a) under suitable conditions to form a pyrone having the structure:

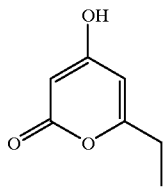

(c) alkylating the pyrone formed in step (b) under suitable conditions to form a pyrone acetal having the structure:

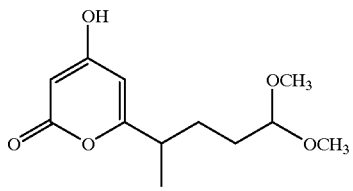

(d) etherifying the pyrone acetal formed in step (c) under suitable conditions to form an ether pyrone acetal having the structure:

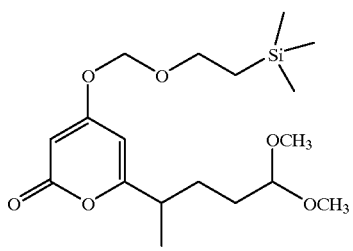

(e) (i) acidolytically cleaving the pyrone acetal under suitable conditions; and (ii) reacting with triethyl phosphonoacetate under suitable conditions to form a protected pyrone ester having the structure:

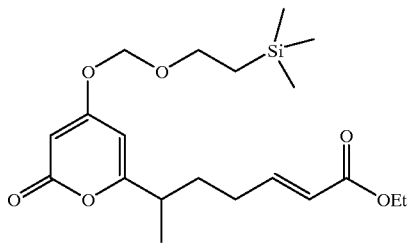

and (f) deprotecting the protected pyrone ester under suitable conditions to form the pyrone ester.

Hydrolysis in step (a) recited above is carried out using a hydroxide base, such as LiOH, NaOH, or KOH, preferably NaOH, followed by acidification with a variety of acids, including, but not limited to, hydrochloric acid, sulfuric acid, phosphoric acid, nitric acid, and TFA, preferably, hydrochloric acid. Dimerization in step (a) is effected using a condensing agent, such as carbonyl diimidazole, or an equivalent reagent known in the art. Hydrolysis step (b) is performed using a strong acid such as hydrochloric acid, hydrobromic, trifluoroacetic or sulfuric acid, preferably 90% sulfuric acid, at elevated temperature, in the range from about 65° C. to about 160° C., preferably between about 100° C. and about 140° C., more preferably, at 130° C. Alkylation step (c) with fluoro-, chloro- or bromopropionaldehyde dimethyl acetal is carried out using a strong base such as n-butyl lithium, t-butyl lithium, sec-butyl lithium or phenyl lithium, in an inert polar aprotic solvent, such as THF in the presence or absence of a co-solvent, such as HMPT. Etherification step (d) is effected using a strong non-nucleophilic base such DIPEA or triethylamine in an inert organic solvent, such as dichloromethane. Acetal cleavage step (e) (i) is carried out using a strong acid, such as sulfuric acid or p-tosic acid, in a solvent mixture preferably comprising THF and water in a ratio of 10:1. Condensation step (e) (ii) employs a strong non-nucleophilic base, such as sodium hydride, in a solvent mixture favorably comprising toluene and DMF. Deprotection step (f) utilizes an organic fluoride salt, preferably tetrabutylammonium fluoride.

The present invention further provides a process of preparing a pyrone ester having the structure:

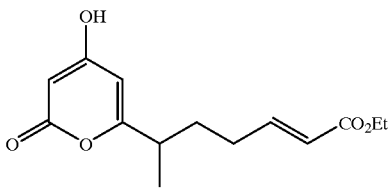

which comprises:

(a) (i) alkylating a pyrone having the structure:

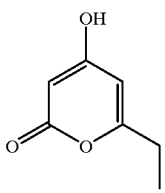

(ii) etherifying the pyrone formed in step (i) under suitable conditions to form protected pyrone having the structure:

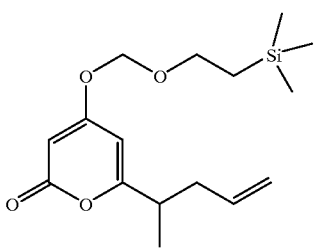

(b) (i) hydroborating the protected pyrone formed in step (a) (ii) under suitable basic conditions; and (ii) oxidizing under suitable conditions to form a pyrone aldehyde having the structure:

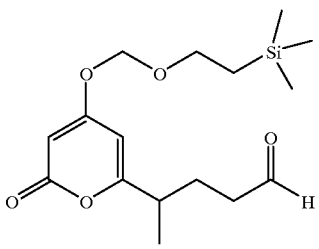

(c) condensing the pyrone aldehyde formed in step (b) (ii) with triethyl phosphonoacetate under suitable conditions to form a protected pyrone ester having the structure:

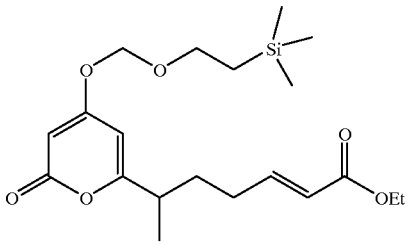

and (d) cleaving the protected pyrone ester under suitable conditions to form the pyrone ester.

As practiced in the invention, aluylation step (a) (i) is effected using allyl chloride, bromide or fluoride as the halide and a strong base, such as sodium hydride or n-butyl lithium, in a polar aprotic solvent mixture favorably made up of THF and HMPT. Protetion step (a) (ii) is carried out using a strong non-nucleophilic base, such as DIPEA or triethylamine, in an inert organic solvent, such as dichloromethane. Hydroboration (b) (i) is performed with a borane complex, such as $BH_3$—$SMe_2$, followed by treatment with hydrogen peroxide and inorganic base, such as NaOH. oxidation (b) (ii) preferably utilizes standard Swern conditions. Condensation step (c) is performed using a strong non-nucleophilic base such as sodium hydride. Deprotection step (d) is effected using a strong acid such as sulfuric acid in the presence of a protic solvent, such as ethanol, and a miscible aprotic organic solvent, such as THF.

Generally, the Wadsworth-Emmons reaction is applied in the pathway leading to both 1 and 9, and tolerates the use of aprotic, anhydrous solvents. While both toluene and THF have been used effectively, higher yields are obtained with THF. The preferred base is NaH although other anhydrous bases are also effective. Other reactions generating carbon-carbon double bonds could be equivalently used. Intermediate ester 16 may alternatively be prepared by an addition reaction involving lithium dimethyl cuprate, or an equivalent organometallic reagent. The reductions of the two esters on the pathway to 1 are both performed with DIBAL, although a number of hydride reagents could have been used. Any aprotic, anhydrous solvent would be permissible as long as its melting point is below $-78°$ C. The reaction proceeds rapidly at $-78°$ C., but may optionally be carried out at temperatures up to $-40°$ C. without untoward consequences. The oxidations on the pathway to 1 have been efficiently performed both under Swern conditions and with DDQ, or any reagent proficient in the oxidation of allylic alcohols or primary alcohols, including, but not limited to, manganese oxide, pyridinium chlorochromate, and pyridinium dichromate. The pathway using DDQ is more effective with unsaturated alcohols. The oxidation reaction is preferably performed using a variety of aprotic, anhydrous solvents.

With respect to the production of the pyrone, ethyl propionylacetate is hydroyzed with aqueous NaOH. The reaction may be carried out using any hydroxylic base. The dimerization of the acid to produce pyrone 5 is preferably effected in aprotic, anhydrous solvents. Other carbonyldiimidazole equivalents (e.g., phosphene) can be similarly used. The hydroysis of the propionyl groups to yield 6 occurs in strong acids, including, but not limited to, hydrochloric acid, phosphoric acid, nitric acid. The alkylation of 6 with either 3-bromopropionaldehyde dimethyl acetal or allyl bromide is preferably performed in the presence of hexamethylphosphoric triamide (HMPT) to help solubilize the anion.

The SEM ether is a preferred protecting group. For the installation step, various amine bases may be used, including, but not limited to, diisopropylethylamine (DIPEA), triethylamine, DBU (1,8-diazbicyclo[5.4.0] undec-7-ene), and pyridine. The reaction may be performed in various polar aprotic solvents, including, but not limited to, chloroform, carbon tetrachloride and dimethyl formamide (DMF). The removal of the dimethyl acetal using dilute $H_2SO_4$ in THF/$H_2O$ may be carried out with mild acids which do not cleave the SEM group. In general, if $H_2O$ is used as a co-solvent rather than an alcohol, the SEM group is not affected. The removal of the SEM group in intermediate 9 to produce compound 10 is effected using either TBAF/DMPU or dilute $H_2SO_4$ in THF/EtOH, acidic conditions being the more effective.

The hydroboration of intermediate 11 is carried out with a number of borane reagents, e.g., $BH_3$·THF or boranedimethyl sulfide complex (FIG. 7). Yields are limited by the reactivity of the pyrone under these conditions. The aldol reaction between compounds 1 and 10 is best performed using TFA in $CH_2Cl_2$. In the alternate route used to attach the 3-position side chain, the acylation of compound 10 with propionyl chloride to produce intermediate 15 proceeds efficiently in the presence of TFA at elevated temperature. Lithium diisopropylamide (LDA) is an efficient base for the aldol reaction of between compounds 14 and 15 yielding intermediate 17. A variety of other bases are also useful for the purpose, including, but not limited to, hydroxide bases, lithium-containing bases and alkoxides.

The present invention provides a process of preparing a myxopyronin having the structure:

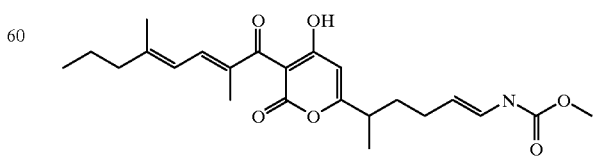

which comprises:

(a) treating an acyl pyrone having the structure:

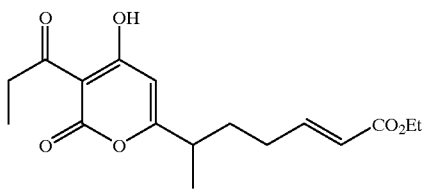

with an unsaturated aldehyde having the structure:

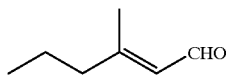

under suitable conditions to form a pyrone aldol having the structure:

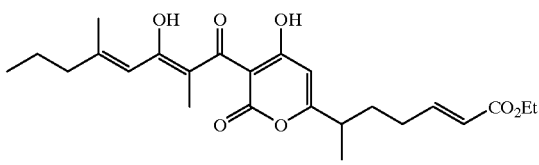

(b) (i) mesylating the pyrone aldol formed in step (a) under suitable conditions to form a pyrone aldol mesylate; and (ii) reacting the pyrone aldol mesylate formed in step (b) (i) under suitable basic conditions to form a pyrone diene having the structure:

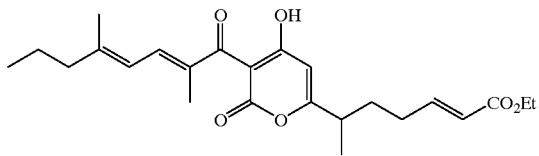

and (c) saponifying the pyrone diene formed in step (b) (ii) under suitable conditions to form a pyrone acid; (d) converting the pyrone acid formed in step (c) under suitable conditions to a pyrone acyl azide; and (e) solvolyzing the pyrone acyl azide formed in step (d) with methanol under suitable conditions to form the myxopyronin.

In one embodiment, the present invention provides a process as disclosed above wherein the acyl pyrone in step (a) is treated with the unsaturated aldehyde in the presence of a Lewis acid catalyst. In a certain embodiment, the present invention provides the process wherein the acid catalyst is titanium tetrachloride/triethylamine combination. In another embodiment, the present invention provides a process as disclosed above wherein the pyrone aldol in step (b) (i) is mesylated with methanesulfonyl (mesyl) chloride in the presence of triethylamine. In another embodiment, the present invention provides a process as disclosed above wherein the pyrone aldol mesylate in step (b) (ii) is reacted with DBU. In another embodiment, the present invention provides a process as above wherein the pyrone diene in step (c) is saponified with lithium hydroxide. In yet another embodiment, the present invention provides a process as above wherein the pyrone acid in step (d) is converted using diphenylphosphoryl azide in the presence of triethylamine.

The aldol condensation of step (a) may be effected at subambient temperatures, preferably at −78° C. Mesylation step (b) (i) is carried out preferably using mesyl chloride but an equivalent reaction sequence would result using another acylating agent, such as p-tosyl chloride, acetic anhydride. Step (b) (i) occurs efficiently in the presence of a non-nucleophilic organic base, such as DIPEA or triethylamine. Elimination step (b) (ii) may be performed using a reagent effective to cause elimination, preferably, a strong non-nucleophilic base such as DBU. Saponifying step (c) is effected using a base such as lithium hydroxide, sodium hydroxide or potassium hydroxide under aqueous or mixed aqueous/dipolar solvent conditions. Converting step (d) is carried out by heating the pyrone acid with diphenylphosphoryl azide, or an equivalent reagent, in the present of a strong non-nucleophilic base, such as triethylamine or diethylisopropylamine, in a noninteracting organic solvent, such as benzene, toluene or xylene, at a temperature above room temperature, preferably at the reflux temperature of the solvent. Solvolyzing step (e) is effected by heating the pyrone acyl azide in methanol at a temperature above room temperature, preferably at the reflux temperature of methanol.

The present invention provides a process of preparing an acyl pyrone having the structure:

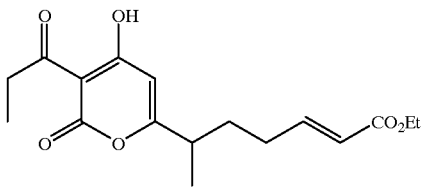

which comprises:

(a) oxidizing a pyrone diol having the structure:

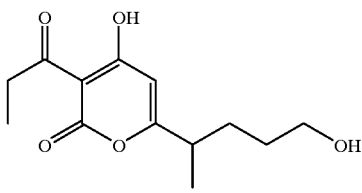

under suitable oxidizing conditions to form a pyrone aldehyde having the structure:

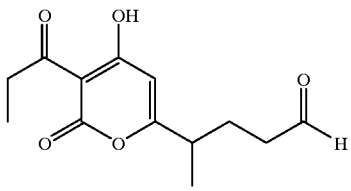

and (b) condensing the pyrone aldehyde formed in step (a) with triethylphosphonoacetate under suitable basic conditions to form the pyrone ester. In one embodiment, the present invention provides a process as shown above wherein the pyrone diol in step (a) is oxidized with a Dess-Martin periodinate. In another embodiment, the present invention provides a process as above wherein the condensing step is effected with sodium hydride.

Oxidizing step (a) is carried out using any oxidant known in the art suited to the purpose, including chromium oxide, pyridinium chlorochromate, dicyclohexylcarbodiimide/ dimethylsulfoxidealuminum oxide/acetone, lead tetraacetate, etc. A preferred oxidant is the Dess-Martin periodinate. Condensing step (b) is effected in the presence of a strong non-nucleophilic base, such as sodium hydride or potassium t-butoxide, in an inert organic solvent such as benzene, toluene, or xylene, typically at ambient temperatures.

The present invention provides a process of preparing a pyrone diol having the structure:

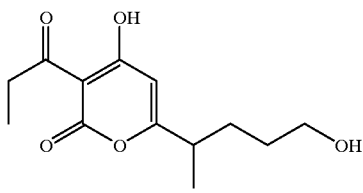

which comprises:
(a) (i) deprotonating an acyl pyrone having the structure:

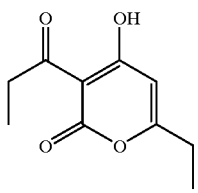

under suitable basic conditions to form an anion; and
(ii) alkylating the anion formed in step (a) (i) with a siloxyalkyl halide having the structure:

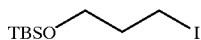

under suitable conditions to form an alkylated pyrone having the structure:

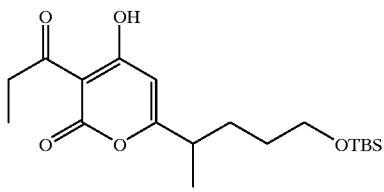

and (b) deprotecting the alkylated pyrone formed in step (a) (ii) under suitable conditions to form the pyrone diol. In one embodiment, the present invention provides a process as disclosed wherein the acyl pyrone in step (a) (i) is deprotonated using lithium diisopropylamide or lithium diethylamide. In another embodiment, the present invention provides a process as above wherein the alkylated pyrone in step (b) is deprotected with a weak acid. In a certain embodiment, the invention provides a process wherein the weak acid is acetic acid.

Deprotonating step (a) (i) is carried out using a strong non-nucleophilic base, such as LDA, lithium diethylamide, potassium t-butoxide, sodium amide, sodium hydride, etc., in a non-interacting organic dipolar solvent or solvent mixture, such as tetrahydrofuran (THF) and/or hexamethylphosphoramide (HMPA), at subambient temperatures, preferably at –78° C. The deprotonated dianion is used directly in the alkylation step (a) (ii) is performed at subambient temperatures, preferably –78° C.

The present invention further provides the following compositions of matter, having the structures set forth below. These compounds are useful as intermediates in the synthesis of myxopyronins and corallopyronins according to the present invention:

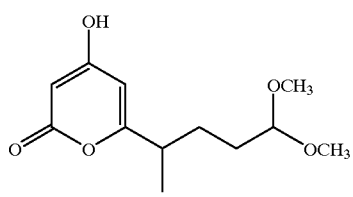

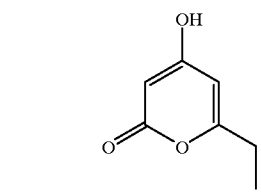

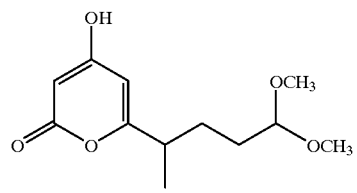

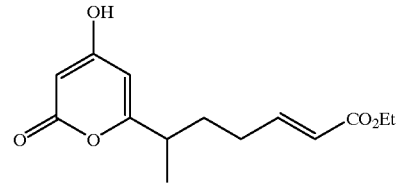

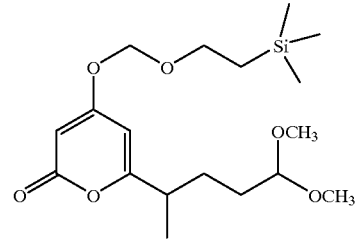

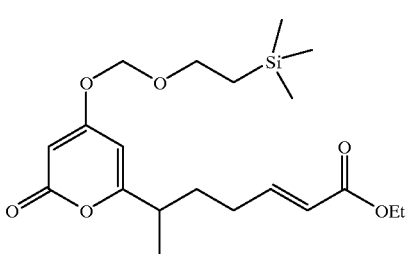

-continued

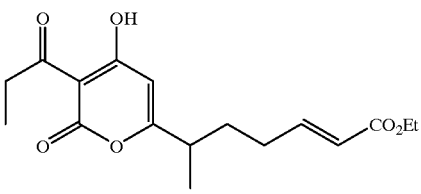

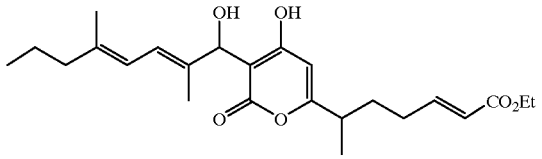

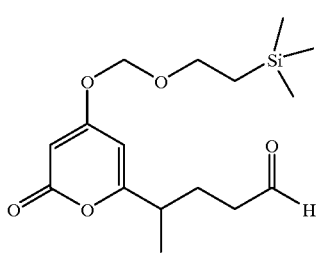

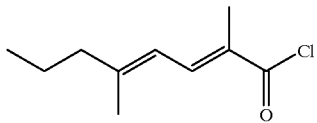

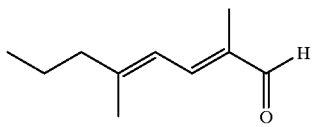

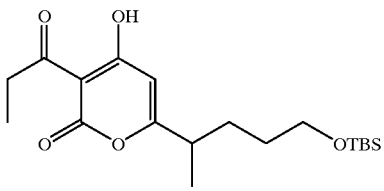

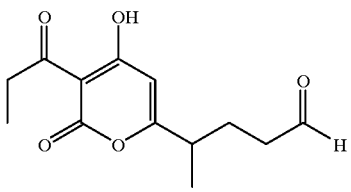

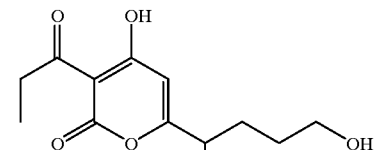

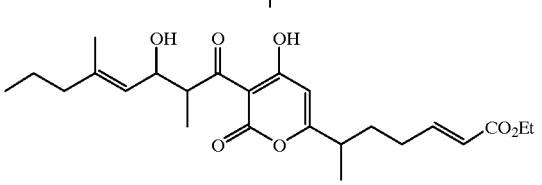

-continued

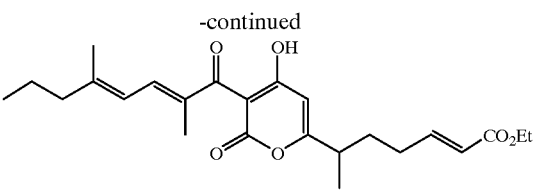

The scope of the present invention includes compositions of matter wherein the $C_\alpha$ carbon at the 6-position of the pyrone ring therein possesses either an R or S absolute configuration, as well as mixtures thereof. The processes of the present invention encompass the use of various alternate protecting groups known in the art. For example, in the preparation of unsaturated aldehyde 1, ethyl ester 16 may be equivalently replaced with a methyl, propyl, isobutyl, phenyl, or benzyl ester, wherein the triethylphosphonoacetate or triethylphosphonopropionate may be replaced with the corresponding alternate ester. Similarly, in the preparation of intermediate pyrone ester 10 and of myxopyronin 18, the ethyl ester may be equivalently replaced with, for example, a methyl, propyl, isobutyl, phenyl, or benzyl ester, wherein the triethylphosphonoacetate used in the conversion from 8 to 9 may be replaced with the corresponding alternate ester. Furthermore, in the conversion from compound 6 to 7, the bromopropionaldehyde dimethyl acetal may be equivalently replaced with, for example, an ethyl, propyl, butyl, ethylene, or propylene acetal, and in the conversion from 7 to 8, SEM-Cl may be equivalently replaced with another protecting group, for example, methoxymethyl, methylthiomethyl, trimethylsilyl, t-butyldimethylsilyl, or tetrahydropyranyl.

The present invention will be better understood from the Experimental Details which follow. However, one skilled in the art will readily appreciate that the specific methods and results discussed are merely illustrative of the invention as described in the claims which follow thereafter.

EXAMPLE 1

Synthesis of 6-ethyl Pyrone

Hydrolysis of the Ethyl Propionylacetate 4

To a flame-dried flask under flushing argon containing 25 gr (175 mmol) of ethyl propionylacetate 4 was added 300 ml of 1.5M NaOH. The solution was stirred at room temperature for 18 hours. Tlc indicated that the starting material was gone. The solution was placed in an ice/$H_2O$ bath and concentrated HCl was added until the pH of the solution was 1. The reaction was allowed to warm to room temperature. The solution was saturated with KCl and extracted with EtOAc (3×100 ml) and $CHCl_3$ (3×100 ml). The combined organic layers were dried with $Na_2SO_4$, filtered and evaporated on a rotary evaporator. This yielded 15.5 gr (76%) of a white solid. The product needed no further purification and was used directly in the next step.

$^1$H NMR (300 MHz, $CDCl_3$): δ 1.1 (3H, t); 2.6 (2H, q); 3.5 (2H, s).

Dimerization of the Acid to Produce the Pyrone 5

To a flame-dried flask under flushing argon containing 10.55 gr (91 mmol, 1 eq) of the acid dissolved in 250 ml of freshly distilled THF was added 16.22 gr (100 mmol, 1.1 eq) of carbonyldiimidazole. The reaction was left to stir for 12 hours. The reaction was concentrated using a rotary evaporator. The residue was partitioned between 100 ml of $CHCl_3$ and 100 ml of 10% HCl. The aqueous layer was extracted with $CHCl_3$ (2×50 ml). The combined organic layers were dried with $Na_2SO_4$, filtered and evaporated on a rotary evaporator. The product needed no further purification as long as it was left on a vacuum pump long enough to remove any remaining starting acid. This yielded 8.8 gr (98%) of 5 a tan solid.

$^1$H NMR (300 MHz, CDCl$_3$): δ 1.15 (3H, t); 1.25 (3H, t); 2.55 (2H, q); 3.1 (2H, q); 5.95 (1H, s).

Removal of the Propionoyl Group to Produce 6

In a round-bottomed flask was placed 11.4 gr (58.2 mmol, 1 eq) of the pyrone 5 and it was dissolved in 50 ml of concentrated H$_2$SO$_4$. The solution was heated to 130° C. in an oil bath for 15 minutes. The reaction was allowed to cool to room temperature. Approximately 50 gr of ice was added with stirring. The solution was extracted with Et$_2$O (3×50 ml). The combined organic layers were dried with Na$_2$SO$_4$, filtered and evaporated on a rotary evaporator. This yielded 7.7 gr (94%) of 6 a tan solid. The product needed no further purification.

$^1$H NMR (300 MHz, CDCl$_3$): δ 1.2 (3H, t); 2.5 (2H, q); 5.65 (1H, d); 6.0 (1H, d).

EXAMPLE 2

Construction of 6-position Side Chain

3-Bromopropionaldehyde Dimethyl Aacetal Approach:

Alkylation of Pyrone with 3-bromopropionaldehyde Dimethyl Acetal to Produce 7

To a flame-dried flask under flushing argon containing 2.5 gr (18 mmol, 1 eq) of the ethyl pyrone 6 dissolved in 40 ml of freshly distilled THF was added 8 ml of HMPT. The solution was slowly cooled to −78° C. in a dry ice/acetone bath, making sure the ethyl pyrone stayed in solution. Once the temperature had equilibrated, 24.6 ml (39 mmol, 2.2 eq) of 1.6 M n-BuLi was added by syringe. The solution quickly became a maroon color. The dry ice/acetone bath was replaced with an ice/H$_2$O bath and the solution allowed to stir for 30 minutes. At this point, the 3-bromopropionaldehyde dimethyl acetal was added by syringe. The solution was left to stir and warm to room temperature overnight. The reaction was quenched by the addition of 25 ml of H$_2$O. Addition of 1% HCl occurred until the solution was acidic. The solution was extracted with Et$_2$O (3×50ml). The combined organic layers were extracted with saturated brine solution, dried with Na$_2$SO$_4$, filtered and evaporated on a rotary evaporator. The product was 7 a brown oil (1.75 gr) and was not purified at this time. It was used directly in the production of the SEM ether.

Conversion of the 4-hydroxyl Group of 7 into the SEM Ether 8

To a flame-dried flask under flushing argon containing 1.75 gr (12 mmol, 1 eq) of the crude alkylation product 7 dissolved in 40 ml of anhydrous CH$_2$Cl$_2$ was added 2.42 ml (12 mmol, 1 eq) of N,N-diisopropylethylamine (DIPEA) by syringe. The solution immediately become orange. The solution was cooled with a ice/H$_2$O bath and 2.46 ml (12 mmol, 1 eq) of 2-(trimethylsilyl)ethoxymethyl chloride (SEM-Cl) was added by syringe. A white vapor formed. The reaction was allowed to stir for 2 hours at which time tlc showed that no starting material remained (5:2 benzene/ethyl acetate). The reaction was diluted with 150 ml of Et$_2$O and the resulting solution extracted with saturated NaHCO$_3$ (2×50 ml). The organic layer was extracted with brine solution (1×50 ml). The organic layer was dried with Na$_2$SO$_4$, filtered and evaporated on a rotary evaporator. The residue was placed on a SiO$_2$ column and eluted with 5:2 benzene/ethyl acetate. This yielded 0.46 gr (7% for the two steps combined) of a light yellow oil 8.

$^1$H NMR (300 MHz, CDCl$_3$): δ 0.0 (9H, s); 1.0 (2H, t); 1.2 (3H, d); 1.5–1.8 (4H, m); 2.5 (1H, m); 3.3 (6H, 2s); 3.7 (2H, t); 4.3 (1H, t); 5.2 (2H, s); 5.6 (1H, d); 5.8 (1H, d).

Deprotection of the Aldehyde

In a round-bottomed flask was placed 0.45 gr (1.2 mmol, 1 eq) of the pyrone 8 and it was dissolved in 22 ml of a 10:1 mixture of THF/H$_2$O. To this solution was added 10 drops of concentrated H$_2$SO$_4$ and the reaction left to stir. After 3 hours, 3 more drops of H$_2$SO$_4$ were added. After 3 additional hours, tlc showed no more starting material (5:2 benzene/ethyl acetate). The reaction was diluted with 20 ml of Et$_2$O and this solution extracted with saturated NaHCO$_3$ (1×10 ml) and brine (1×10 ml). The organic layer was dried with Na$_2$SO$_4$, filtered and evaporated on a rotary evaporator. This yielded 0.39 gr (>98%) of a light yellow oil 12. The product needed no further purification.

$^1$H NMR (300 MHz, CDCl$_3$): δ 0.0 (9H, s); 1.0 (2H, t); 1.2 (3H, d); 1.8–2.0 (4H, m); 2.6 (1H, m); 3.7 (2H, t); 5.2 (2H, s); 5.6 (1H, d); 5.8 (1H, d) 9.75 (1H, t)

Horner-Emmons-Wadsworth Reaction of the Deprotected Aldehyde to Produce 9

To a flame-dried flask under flushing argon containing 0.236 ml (1.2 mmol, 1 eq) of the triethyl phosphonoacetate dissolved in 15 ml of freshly distilled toluene was added 50 mg (1.24 mmol, 1.05 eq) of NaH as a 60% mineral oil dispersion. Hydrogen evolution was witnessed. Once this subsided, 0.40 gr (1.2 mmol, 1 eq) of the aldehyde dissolved in toluene (3 ml) was added by syringe. The syringe was washed with an additional 2 ml of toluene and the solution added to the reaction. Almost immediately, an orange oil came out of solution. The reaction was left to stir overnight. The reaction was stopped by the addition of 20 ml of H$_2$O and the solution made acidic with 1% HCl. The solution was extracted with Et$_2$O (3×10 ml). The combined organics were extracted with saturated NaHCO$_3$ (1×10 ml) and brine (1×10 ml). The organic layer was dried with Na$_2$SO$_4$, filtered and evaporated on a rotary evaporator. The residue was placed on a SiO$_2$ column and eluted with 2:1 hexane/ethyl acetate. This yielded 0.347 gr (74%) of a clear oil 9.

$^1$H NMR (300 MHz, CDCl$_3$): δ 0.0 (9H, s); 0.9 (2H, t); 1.25 (3H, d); 1.25 (3H, t); 1.6 (2H, m); 1.9 (1H, m); 2.2 (2H, m); 2.6 (1H, m); 3.7 (2H, t); 4.2 (2H, q); 5.2 (2H, s); 5.6 (1H, d); 5.8 (1H, d); 5.85 (1H, d); 6.9 (1H, dt)

EXAMPLE 3

Allyl Bromide Approach:

Allylation of Ethyl Pyrone 6

To a flame-dried flask under flushing argon containing 0.108 gr (0.77 mmol, 1 eq) of the ethyl pyrone 6 dissolved in 20 ml of freshly distilled THF was added 2 ml of HMPT. The solution was slowly cooled to −78° C. in a dry ice/acetone bath, making sure the ethyl pyrone stayed in solution. Once the temperature had equilibrated, 1.06 ml (1.7 mmol, 2.2 eq) of 1.6 M n-BuLi was added by syringe. The solution quickly became a maroon color. The dry ice/acetone bath was replaced with an ice/H$_2$O bath and the solution allowed to stir for 2 hours. At this point, the allyl bromide was added by syringe. As the end of the addition was reached, the color of the solution became almost yellow. The reaction was allowed to stir for 1 hour. The contents of the reaction were partitioned between Et$_2$O and 1N HCl (25 ml of each). The layers were separated and the aqueous was extracted with Et$_2$O (2×25 ml). The organics were combined and extracted with 25 ml of saturated KCl. The organic layer was dried with Na$_2$SO$_4$, filtered and evaporated on a rotary evaporator. This yielded 0.110 gr (76%) of a light yellow oil. The product needed no further purification.

$^1$H NMR (300 MHz, CDCl$_3$): δ 1.2 (3H, d); 2.25 (1H, m); 2.45 (1H, m); 2.6 (1H, m); 5.0 (1H, s); 5.05 (1H, d); 5.6 (1H, d); 5.7 (1H, m); 5.9 (1H, d).

Conversion of the 4-hydroxyl Group into the SEM Ether 11

To a flame-dried flask under flushing argon containing 0.110 gr (0.61 mmol, 1 eq) of the crude alkylation product dissolved in 3 ml of anhydrous $CH_2Cl_2$ was added 0.106 ml (0.61 mmol, 1 eq) of N,N-diisopropylethylamine (DIPEA) by syringe. The solution immediately become orange. The solution was cooled with a ice/$H_2O$ bath and 0.108 ml (0.61 mmol, 1 eq) of 2-(trimethylsilyl)ethoxymethyl chloride (SEM-Cl) was added by syringe. A white vapor formed. The reaction was allowed to stir for 2 hours at which time tlc showed that no starting material remained (3:1 hexane/ethyl acetate). The reaction was diluted with 15 ml of $Et_2O$ and the resulting solution extracted with saturated $NaHCO_3$ (2×5 ml). The organic layer was extracted with brine solution (1×5 ml). The organic layer was dried with $Na_2SO_4$, filtered and evaporated on a rotary evaporator. The residue was placed on a $SiO_2$ column and eluted with 3:1 hexane/ethyl acetate. This yielded 0.83 gr (45%) of a clear oil 11.

$^1$H NMR (300 MHz, $CDCl_3$): δ 0.0 (9H, s); 0.9 (2H, t); 1.2 (3H, d); 2.25 (1H, m); 2.45 (1H, m); 2.6 (1H, m); 3.7 (2H, t); 4.2 (2H, q); 5.0 (1H, s); 5.05 (1H, d); 5.2 (2H, s); 5.6 (1H, d); 5.7 (1H, m); 5.8 (1H, d).

Hydroboration of the Allyl Group

To a flame-dried flask under flushing argon containing 0.74 gr (2.4 mmol, 1 eq) of the allylation product 11 dissolved in 20 ml of freshly distilled THF and cooled to 0° C. in an ice/$H_2O$ bath was added 1.25 ml (2.5 mmol, 1.05 eq) of BH$_3$THF by syringe. The reaction was allowed to stir for two hours at which time tlc indicated the reaction was finished. The reaction was stopped by sequential addition of 8 ml of methanol, 3 ml of 5M NaOH and 3 ml of 30% $H_2O_2$. The solution was acidified to pH 4 with 1% HCl and extracted with $Et_2O$ (3×20 ml). The combined organic layers were dried with $Na_2SO_4$, filtered and evaporated on a rotary evaporator. The residue was placed on a $SiO_2$ column and eluted with 2:1 ethyl acetate/toluene. This yielded 0.30 gr (38%) of a clear oil.

$^1$H NMR (300 MHz, $CDCl_3$): δ 0.0 (9H, s); 0.9 (2H, t); 1.25 (3H, d); 1.5–1.8 (4H, m); 2.55 (1H, m); 2.45 (1H, m); 2.6 (1H, m); 3.65 (2H, t); 3.75 (2H, t); 5.2 (2H, s); 5.6 (1H, d); 5.8 (1H, d).

Swern Oxidation of the Alcohol to Produce 12

A flame-dried flask under flushing argon containing 0.105 ml (1.5 mmol, 2.55 eq) of DMSO dissolved in 5 ml of anhydrous $CH_2Cl_2$ was cooled to −78° C. in a dry ice/acetone bath. To this solution was added 0.058 ml (0.64 mmol, 1.14 eq) of oxalyl chloride by syringe. The solution was allowed to stir for 5 minutes. 0.19 gr (0.58 mmol, 1 eq) of the alcohol dissolved in 5 ml of anhydrous $CH_2Cl_2$ was added to the solution slowly over the course of 5 minutes. The solution was allowed to stir for 30 minutes. The reaction was terminated by the addition of 0.209 ml (1.5 mmol, 2.6 eq) of triethylamine and stirring for 5 minutes before allowing the solution to warm to room temperature. The solution was diluted with 10 ml of $H_2O$ and the aqueous and organic layers separated. The aqueous layer was extracted with $CH_2Cl_2$ (2×10 ml). The combined organic layers were dried with $Na_2SO_4$, filtered and evaporated on a rotary evaporator. The residue was placed on a $SiO_2$ column and eluted with 2:1 toluene/ethyl acetate. This yielded 0.15 gr (80%) of a clear oil 12. $^1$H NMR showed this compound identical to the aldehyde prepared using the 3-bromopropionaldehyde dimethyl acetal pathway.

Horner-Emmons-Wadsworth Reaction of the Aldehyde

To a flame-dried flask under flushing argon in an ice/$H_2O$ bath containing 0.223 gr (1.1 mmol, 1.05 eq) of the triethyl phosphonoacetate dissolved in 15 ml of freshly distilled THF was added 45 mg (1.1 mmol, 1.05 eq) of NaH as a 60% mineral oil dispersion. Once hydrogen evolution subsided, the aldehyde dissolved in THF (3 ml) was added by syringe. The syringe was washed with an additional 2 ml of THF and the solution added to the reaction. Almost immediately, an orange oil came out of solution. The reaction was left to stir overnight. The reaction was quenched by the addition of 20 ml of $H_2O$ and the solution made acidic with 1% HCl. The solution was extracted with $Et_2O$ (3×10 ml). The combined organics were extracted with saturated $NaHCO_3$ (1×10 ml) and brine (1×10 ml). The organic layer was dried with $Na_2SO_4$, filtered and evaporated on a rotary evaporator. The residue was placed on a $SiO_2$ column and eluted with 2:1 hexane/ethyl acetate. This yielded 0.39 gr (92%) of a clear oil. $^1$H NMR showed this compound identical to the HEW adduct prepared using the 3-bromopropionaldehyde dimethyl acetal pathway.

Removal of the SEM Protecting Group to Produce 10

In a round-bottomed flask was placed 0.55 gr (1.4 mmol, 1 eq) of the pyrone and it was dissolved in (33 ml of a 10:1 mixture of THF/EtOH. To this solution was added 30 drops of concentrated $H_2SO_4$ and the reaction left to stir. After 6 hours, tlc indicated no starting material. The reaction was diluted with 30 ml of ethyl acetate. The solution was extracted with saturated $NaHCO_3$ (3×20 ml). The aqueous layer was acidified to <pH 4 with 10% HCl. The solution was extracted with ethyl acetate (3×30 ml). The combined organic layers were dried with $Na_2SO_4$, filtered and evaporated on a rotary evaporator. This yielded 0.37 gr (>98%) of a clear oil 10. The product needed no further purification.

$^1$H NMR (300 MHz, $CDCl_3$): δ 1.25 (3H, d); 1.25 (3H, t); 1.7 (1H, m); 1.9 (1H, m); 2.2 (2H, m); 2.6 (1H, m); 4.2 (2H, q); 5.5 (1H, d); 5.8 (1H, d); 5.95 (1H, d); 6.9 (1H, dt).

EXAMPLE 4

Synthesis of the 3-position sidechain: Horner-Emmons-Wadsworth Reaction of 2-pentanone with Triethyl Phosphonoacetate To a flame-dried flask under flushing argon in an ice/$H_2O$ bath containing 7.48 ml (37.7 mmol, 1. eq) of the triethyl phosphonoacetate dissolved in 100 ml of freshly distilled toluene was added 0.95 gr (40 mmol, 1.05 eq) of NaH as a 60% mineral oil dispersion. Once hydrogen evolution subsided, 2-pentanone was added. Almost immediately, an orange oil came out of solution. The reaction was left to stir overnight. The reaction was quenched by the addition of 50 ml of $H_2O$ and the solution made acidic with 1% HCl. The solution was extracted with $Et_2O$ (3×20 ml). The combined organics were extracted with saturated $NaHCO_3$ (1×10 ml) and brine (1×10 ml). The organic layer was dried with $Na_2SO_4$, filtered and evaporated on a rotary evaporator. The residue was placed on a $SiO_2$ column and eluted with 15:1 hexane/ethyl acetate. This yielded 4.9 gr (83%) of a clear oil.

$^1$H NMR (300 MHz, $CDC_3$): δ 0.9 (3H, t); 1.25 (3H, t); 1.5 (2H, m); 2.1 (2H, t) 2.15 (3H, s); 4.15 (2H, q); 5.65 (1H, s).

Alternate Synthesis of the Unsaturated Ester 16

To a flask containing 45.7 gr (240 mmol, 1 eq) of CuI suspended in 240 ml of diethyl ether cooled to 0° C. with an ice/$H_2O$ bath was added 343 ml (480 mmol, 2 eq) of a 1.4M solution of MeLi over the course of 1 hour. The solution was stirred for 5 minutes at 0° C. and then cooled to −78° C. with a dry ice/acetone bath. Initially, a yellow precipitate formed upon the addition of the MeLi but it solubilized with time.

In a second flask, 18.98 gr (120 mmol, 1 eq) of ethylbutyryl acetate in 160 ml of diethyl ether was added to a suspension of 5.28 gr (132 mmol, 1.1 eq) of NaH in 80 ml of diethyl ether cooled to 0° C. over the course of 1 hour. The slurry that formed was stirred for 20 minutes at 0° C. 19.1 ml (132 mmol, 1.1. eq) of diethylphosphorochloridate was added over the course of 10 minutes. The solution was stirred at room temperature for 2 hours and then poured into 200 ml of ice/saturated $NH_4Cl$. The aqueous and organic layers were separated. The organic layer was washed with 300 ml of saturated $NaHCO_3$. The organic layer was dried with $Na_2SO_4$, filtered and evaporated on a rotary evaporator. This yielded the 35.4 gr of the enol phosphonate which was used without further purification. The enol phosphonate was dissolved in 120 ml of diethyl ether and added to the first flask containing $LiMe_2Cu$ over the course of 20 minutes with the solution was being cooled to −78° C. The solution was stirred for 2.5 hours while being cooled at −78° C. The solution was poured into 300 ml of saturated $NH_4Cl$. The aqueous and organic layers were separated. The organic layer was washed with 2×200 ml of saturated $NaHCO_3$ and 300 ml of brine solution. The organic layer was dried with $Na_2SO_4$, filtered and evaporated on a rotary evaporator. This yielded 17 gr of a light green liquid that was distilled to give 10.4 gr (55%) yield of a colorless oil. The NMR was identical to that of 16 but contained a 10:1 ratio of E/Z isomers.

DIBAL Reduction of the Ethyl Ester

A flame-dried flask under flushing argon containing 4.9 gr (31.4 mmol, 1 eq) of the ethyl ester dissolved in 100 ml of freshly distilled THF was cooled to −78° C. with a dry ice/acetone bath. 78.5 ml (78.5 mmol, 2.5 eq) of a 1.0M solution of DIBAL was dripped into the solution by syringe over the course of 10 minutes. The solution was left to stir for 1 hour. Fifty milliliters of methanol were poured into the solution to quench the excess DIBAL. The solution was diluted with 200 ml of $H_2O$. 200 ml of $Et_2O$ was added to the solution followed by 100 ml of 5% HCl. The whole solution was poured into a separatory funnel and the aqueous and organic layers separated. The aqueous layer was extracted with $Et_2O$ (2×50 ml). The combined organic layers were dried with $Na_2SO_4$, filtered and evaporated on a rotary evaporator. The residue was placed on a $SiO_2$ column and eluted with 3:1 hexane/ethyl acetate. This yielded 1.2 gr (34%) of a clear oil.

$^1$H NMR (300 MHz, $CDCl_3$): δ 0.85 (3H, t); 1.4 (2H, m); 1.65 (3H, s); 1.9 (2H, t); 4.1 (2H, d); 5.4 (1H, t).

Swern Oxidation of the Alcohol to Produce 14

A flame-dried flask under flushing argon containing 1.9 ml (26.8 mmol, 2.55 eq) of DMSO dissolved in 30 ml of anhydrous $CH_2Cl_2$ was cooled to −78° C. in a dry ice/acetone bath. To this solution was added 1.05 ml (12 mmol, 1.14 eq) of oxalyl chloride by syringe. The solution was allowed to stir for 5 minutes. 1.2 gr (10.5 mmol, 1 eq) of the alcohol dissolved in 10 ml of anhydrous $CH_2Cl_2$ was added to the solution slowly over the course of 5 minutes. The syringe was washed with 10 ml of $CH_2Cl_2$ and this solution added to the reaction. The solution was allowed to stir for 30 minutes. The reaction was stopped by the addition of 3.81 ml (27.3 mmol, 2.6 eq) of triethylamine and stirring for 5 minutes before allowing the solution to warm to room temperature. The solution was diluted with 20 ml of $H_2O$ and the aqueous and organic layers separated. The aqueous layer was extracted with $CH_2Cl_2$ (2×10 ml). The combined organic layers were extracted with brine solution, dried with $Na_2SO_4$, filtered and evaporated on a rotary evaporator. The residue was placed on a $SiO_2$ column and eluted with 2:1 toluene/ethyl acetate. This yielded 0.45 gr (38%) of a clear oil 14.

$^1$H NMR (300 MHz, $CDCl_3$): δ 0.9 (3H, t); 1.55 (2H, m); 2.15 (3H, s); 2.2 (2H, t); 5.9 (1H, d); 10.0 (1H, d).

Horner-Emmons-Wadsworth Reaction of 14 with Triethyl 2-phosphonopropionate

To a flame-dried flask under flushing argon in an ice/$H_2O$ bath containing 0.86 ml (4.0 mmol, 1 eq) of the triethyl 2-phosphonopropiontate dissolved in 100 ml of freshly distilled toluene was added 0.10 gr (4.2 mmol, 1.05 eq) of NaH as a 60% mineral oil dispersion. Once hydrogen evolution subsided, the aldehyde 14 was added. Almost immediately, an orange oil came out of solution. The reaction was left to stir overnight. The reaction was stopped by the addition of 20 ml of $H_2O$ and the solution made acidic with 10% HCl. The solution was extracted with $Et_2O$ (3×20 ml). The combined organics were extracted with saturated $NaHCO_3$ (1×10 ml) and brine (1×10 ml). The organic layer was dried with $Na_2SO_4$, filtered and evaporated on a rotary evaporator. The residue was placed on a $SiO_2$ column and eluted with 11:1 hexane/ethyl acetate. This yielded 0.385 gr (50%) of a clear oil.

$^1$H NMR (300 MHz, $CDCl_3$): δ 0.9 (3H, t); 1.3 (3H, t); 1.5 (2H, m); 1.85 (3H, s); 1.95 (3H, s); 2.15 (2H, t) 4.15 (2H, q); 6.1 (1H, d); 7.5 (1H, d).

DIBAL Reduction of the Ethyl Ester

A flame-dried flask under flushing argon containing 1.86 gr (9.5 mmol, 1 eq) of the ethyl ester dissolved in 40 ml of freshly distilled THF was cooled to −78° C. with a dry ice/acetone bath. 23.7 ml (23.7 mmol, 2.5 eq) of a 1.0M solution of DIBAL was dripped into the solution by syringe over the course of 5 minutes. The solution was left to stir for 2 hours. An additional 5 ml of DIBAL was added. One hour later, 20 ml of methanol was poured into the solution to quench the excess DIBAL. The solution was diluted with 50 ml of $H_2O$. Fifty milliliters of $Et_2O$ were added to the solution followed by 25 ml of 5% HCl. The whole solution was poured into a separatory funnel and the aqueous and organic layers separated. The aqueous layer was extracted with $Et_2O$ (2×20 ml). The combined organic layers were dried with $Na_2SO_4$, filtered and evaporated on a rotary evaporator. The residue was placed on a $SiO_2$ column and eluted with 3:1 hexane/ethyl acetate. This yielded 1.32 gr (91%) of a clear oil.

$^1$H NMR (300 MHz, $CDCl_3$): δ 0.9 (3H, t); 1.45 (2H, m); 1.75 (3H, s); 1.8 (3H, s); 2.05 (2H, t); 4.1 (2H, d); 6.0 (1H, d); 6.25 (1H, d).

DDQ Oxidation of the Alcohol to the Aldehyde 1

To a flame-dried flask under flushing argon containing 0.7576 gr (4.9 mmol, 1 eq) of the alcohol dissolved in 25 ml of freshly distilled THF was added 2.26 gr (25 mmol, 2 eq) of DDQ. The reaction was allowed to stir for 2 hours. At this point, 5 gr of $SiO_2$ were added and the volatiles evaporated on a rotary evaporator. The resulting solid was placed on top of a $SiO_2$ column and the product eluted with 7:1 hexanes/ ethyl acetate. This yielded 0.39 gr (52%) of a clear oil 1.

$^1$H NMR (300 MHz, $CDCl_3$): δ 0.9 (3H, t); 1.55 (2H, m); 1.85 (3H, s); 1.95 (3H, s); 2.2 (2H, t) 6.3 (1H, d); 7.1 (1H, d); 9.45 (1H, s).

EXAMPLE 5

Attachment of the 3-position Side Chain: Acid-catalyzed Aldol Reaction between Pyrone 10 and Aldehyde To a flame-dried flask under flushing argon containing 0.172 gr (650 μmol, 1 eq) of the pyrone 10 dissolved in 20 ml of anhydrous $CH_2Cl_2$ was added 34 μl (325 μmol, 0.5 eq) of TFA along with 1 gr of 4 Å sieves. The reaction was allowed to stir for 5 minutes. At this point, 100 μl (650 μl, 1 eq) of the aldehyde 1 was added. The reaction was capped and heated at 45° C. for 24 hours. An additional equivalent of TFA was added along with 2 ml of $CH_2Cl_2$. The reaction was heated for an additional 12 hours. The reaction was filtered. One gram of $SiO_2$ was added to the solution and the solvent evaporated. The product became adsorbed onto the $SiO_2$. The resulting solid was applied to the top of a $SiO_2$ column and eluted successively with 7:1 hexane/ethyl acetate, 2:1 hexane/ethyl acetate, 10:1 ethyl acetate/chloroform with 2 drops of acetic acid for every 6 ml of eluent. This yielded 45 mg of the aldehyde, 1.5 mg of the product (1%) 13 and 75 mg of the pyrone.

$^1$H NMR (300 MHz, $CDCl_3$): δ 0.85 (3H, t); 1.2 (3H, d); 1.25 (3H, t); 1.55 (2H, m); 1.65 (1H, m); 1.7 (3H, s); 1.75 (3H, s); 1.9 (1H, m); 2.05 (2H, t); 2.15 (2H, t); 2.55 (1H, m); 4.15 (2H, q); 5.4 (1H, d); 5.5 (1H, d); 5.75 (1H, s); 5.8 (1H, d); 6.2 (1H, s); 6.9 (1H, m).

Acylation of Pyrone 10 with Propionyl Chloride

To a flame-dried flask under flushing argon containing 35 mg (130 μmol, 1 eq) of the pyrone 10 dissolved in 1 ml of anhydrous TFA was added 23 μl (260 μmol, 2 eq) of propionyl chloride. The reaction was heated to 50° C. for 1 hour. An additional 4 equivalents of propionyl chloride were added and the reaction was heated for 12 hours. An additional 4 equivalents of propionyl chloride were added and the reaction was heated for 3 hours. The reaction was partitioned between $H_2O$ and ethyl acetate. The aqueous layer was extracted again with ethyl acetate and the organic layers were combined. The combined organic layers were dried with $Na_2SO_4$, filtered and evaporated on a rotary evaporator. The residue was placed on a $SiO_2$ column and eluted with 2:1 hexane/ethyl acetate. This yielded 21 mg (50%) of a light orange oil 15.

$^1$H NMR (300 MHz, $CDCl_3$): δ 1.15 (3H, t); 1.25 (3H, d); 1.25 (3H, t); 1.7 (1H, m); 1.9 (1H, m); 2.2 (2H, q); 2.6 (1H, m); 3.1 (2H, q); 4.2 (2H, q); 5.8 (1H, d); 5.95 (1H, s); 6.9 (1H, dt).

Base-catalyzed Aldol Reaction between Pyrone and Aldehyde to Produce 17

To a flame-dried flask in a −78° C. dry ice/acetone bath under flushing argon containing 21 mg (65 μmol, 1 eq) of the pyrone 15 dissolved in 3 ml of freshly distilled THF was added 2.9 ml (230 μmol, 3.6 eq) of 0.08M LDA by syringe. The reaction went from a light orange to a dark orange. The reaction was allowed to stir for 30 minutes. The aldehyde was added by syringe. The color of the solution became just a little lighter. After stirring for 90 minutes, the reaction was quenched by addition of saturated $NH_4Cl$ solution. Ten milliliters of ethyl acetate were added to dilute the solution. 1% HCl solution was used to make the solution acidic. The aqueous and organic layers were separated. The aqueous layer was extracted with ethyl acetate (2×5 ml). The combined organic layers were dried with $Na_2SO_4$, filtered and evaporated on a rotary evaporator. The residue was placed on a $SiO_2$ column and eluted with 4:4:1 hexane/ethyl acetate/methanol. This yielded 2 mg (8%) of a light yellow oil 17.

$^1$H NMR (300 MHz, $CDCl_3$): δ 0.9 (3H, t); 1.25 (3H, d); 1.25 (3H, t); 1.5 (2H, m); 1.7 (1H, m); 1.85 (3H, t); 1.9 (1H, m); 1.95 (3H, t); 2.15 (2H, t); 2.2 (2H, t); 2.6 (1H, m); 4.2 (2H, q); 5.8 (1H, d); 5.95 (1H, s); 6.15 (1H, d); 6.9 (1H, dt); 7.0 (1H, d).

Hydrolysis of the Ester 17 to the Acid

To a round-bottomed flask containing 4.0 mg (10 μmol, 1 eq) of the pyrone ester 17 dissolved in 5 ml of 2:2:1 methanol/THF/$H_2O$ is added 4 mg (100 μmol, 10 eq) of LiOH $H_2O$. The solution is stirred at room temperature for 6 hours. The volatiles are evaporated on the rotary evaporator. Any remaining base is quenched by the addition of 1% HCl solution. The aqueous solution is extracted with ethyl acetate (3×10 ml). The combined organic layers are dried with $Na_2SO_4$, filtered and evaporated on a rotary evaporator. 2 mg of an oily yellow residue is isolated and the residue is used in the next step without any further purification.

$^1$H NMR (300 MHz, $CDCl_3$): δ 0.9 (3H, t); 1.25 (3H, d); 1.5 (2H, m); 1.7 (1H, m); 1.85 (3H, t); 1.9 (1H, m); 1.95 (3H, t); 2.15 (2H, t); 2.2 (2H, t); 2.6 (1H, m); 5.8 (1H, d); 5.95 (1H, s); 6.15 (1H, d); 6.95 (1H, dt); 7.0 (1H, d).

Curtius Sequence

To a flame-dried flask under flushing argon containing 2 mg (5.4 μmol, 1 eq) of the residue from the hydrolysis dissolved in 1 ml of acetone is added 1.8 μl (13 μmol, 2.4 eq) of DIPEA. The solution is cooled to 0° C. using an ice/$H_2O$ bath. A solution of 0.83 μl (11 μmol, 2 eq) of methyl chloroformate dissolved in acetone is added dropwise over 30 minutes. After the reaction stirs for 30 minutes, a solution of 1.4 mg (2.2 mmol, 4.0 eq) of $NaN_3$ dissolved in $H_2O$ was added. The solution is stirred for 15 minutes and then poured into 30 ml of ice $H_2O$. The acyl azide is extracted with 6–2 ml portions of toluene. The combined organic layers are dried with $Na_2SO_4$, filtered and concentrated to 2 ml on a rotary evaporator. This solution is added slowly over the course of 15 minutes to a vigorously refluxing solution of 250 μl of methanol in 1 ml dry toluene. Reflux is maintained for 30 minutes and the volatiles are evaporated on a rotary evaporator. The residue is placed on a $SiO_2$ prep plate and eluted with 95:5 $CH_2Cl_2$/methanol. This yields 0.5 mg of a light yellow oil 18.

$^1$H NMR (300 MHz, $CDCl_3$): δ 0.9 (3H, t); 1.25 (3H, d); 1.5 (2H, m); 1.7 (1H, m); 1.85 (3H, t); 1.9 (1H, m); 1.95 (3H, t); 2.15 (2H, t); 2.2 (2H, t); 2.6 (1H, m); 3.7 (3H, s); 4.9 (1H, m); 5.95 (1H, s); 6.15 (1H, d); 6.4 (1H, m); 7.0 (1H, d).

EXAMPLE 6

Modified Curtius Rearrangement

Compound 17a (35 mg, 0.09 mmol), diphenylphosphoryl azide (124 mg, 0.45 mmol) and $Et_3N$ (63 μL, 0.45 mmol) was dissolved in $C_6H_6$ (8.0 mL) and refluxed for 9.0 h. The reaction mixture was cooled to RT, and anhydrous MeOH (2.0 mL) was added. The reaction was warmed to reflux for 6.0 h, then the reaction mixture was concentrated directly in vacuo. The remaining organic residue was flash chromatographed (30% EtOAc in hexanes eluant) to provide (±)myxopyronin A (26.6 mg, 71% yield) as a yellow oil. $^1$H NMR (300 MHz, $CDCl_3$): δ 7.0 (d, J=11.6 Hz, 1H); 6.47 (m, 1H); 6.23 (m, 1H); 6.16 (d, J=11.5 Hz, 1H); 5.94 (s, 1H); 4.94 (m, 1H); 3.72 (s, 3H); 2.6 (m, 1H); 2.15 (t, J=7.7 Hz, 2H); 2.05 (m, 2H); 2.01 (s, 3H); 1.85 (s, 3H); 1.76 (m, 1H); 1.57 (m, 1H); 1.51 (m, 1H); 1.25 (d, J=6.8 Hz, 3H); 0.92 (t, J=7.3 Hz, 3H). $^1$H NMR (300 MHz, $CD_3OD$): δ 7.15 (d, J=12.0 Hz, 1H); 6.39 (d, J=14.2 Hz, 1H); 6.27 (d, J=12.0 Hz, 1H); 6.10 (s, 1H); 5.03 (dt, J=7.1, 14.0 Hz, 1H); 3.66 (s, 3H); 2.68 (m, 1H); 2.19 (t, J=7.4 Hz, 2H); 2.01 (m, 2H); 1.93 (s, 3H); 1.81 (s, 3H); 1.76 (m, 1H); 1.59 (m, 1H); 1.52 (m, 2H); 1.25 (d, J=6.9 Hz, 3H); 0.92 (t, J=7.2 Hz, 3H). MS (FABMS): (M+H) calc. 418, anal. 418. IR (Film, KBr): $v_{max}$=3318 m (b), 2966 s, 2931 s, 2872 m, 1736 s, 1719 s, 1684 m, 1637 s, 1560 s, 1542 s, 1525 s, 1437 m, 1378 m, 1237 m, 1049 m. UV (methanol): $\lambda_{max}$ (log ε): 224 nm (4.17), 295 nm (4.04).

Saponification of Pyrone Ester 17

To a round-bottomed flask containing 25.8 mg (62 μmol, 1 equiv) of the pyrone ester 17 dissolved in 5 mL of 2:2:1 methanol/THF/$H_2O$ was added 26 mg (620 μmol, 10 equiv) of LiOH $H_2O$. The solution is stirred at RT for 24 h. The reaction was quenched by the addition of 1% HCl solution. The aqueous solution is extracted with ethyl acetate (3×10 mL). The combined organic layers are dried with $Na_2SO_4$, filtered and evaporated in vacuo to provide 25 mg of an oily yellow residue. The residue (compound 17a) was isolated used in the next step without any further purification. Since it was crude, compound 17a was not fully characterized. $^1$H NMR (400 MHz, CDCl$_3$): δ 7.03 (dt, J=6.9, 15.7 Hz, 1H); 7.00 (d, J=11.7 Hz, 1H); 6.16 (d, J=11.6 Hz, 1H); 5.96 (s, 1H); 5.85 (d, J=15.7 Hz, 1H); 2.61 (m, 1H); 2.25 (m, 2H); 2.15 (t, J=7.6 Hz, 2H); 2.00 (s, 3H); 1.91 (m, 1H); 1.85 (s, 3H); 1.69 (m, 1H); 1.49 (m, 2H); 1.27 (d, J=6.9 Hz, 3H); 0.91 (t, J=7.3 Hz, 3H). MS (FABMS): (M+H) calc. 389, anal. 389. IR (Film, KBr): $v_{max}$=3436 m (b), 2966 s, 2931 s, 2872 m, 1731 s, 1713 s, 1613 s, 1548 s (b), 1443 m, 1384 m, 1255 m.

Preparation of Allyl Alcohol 14

To a solution of freshly distilled COCl$_2$ (480 μL, 5.5 mmol) in CH$_2$Cl$_2$ (15 mL) was added DMSO (850 μL, 12 mmol) at −78° C. The reaction mixture was stirred at −78° C. for 30 min, then the starting alcohol 13a (570 mg, 5.0 mmol, dissolved in 3.0 mL CH$_2$Cl$_2$, plus 2.0 mL wash) was added. This whole reaction mixture was stirred at −78° C. for another 30 min then Et$_3$N (3.5 mL, 25 mmol) was added. The reaction was stirred for 1.0 h at −78° C., then warmed to RT for 1.0 h before being quenched by H$_2$O. The reaction mixture was extracted with CH$_2$Cl$_2$ (2×80 mL), dried (MgSO$_4$), filtered and concentrated in vacuo to afford the crude aldehyde. The crude product was purified by flash chromatography (10% EtOAc in hexanes eluant) to provide viscous aldehyde 14 (548 mg, 98% yield) as a colorless oil. $^1$H NMR (400 MHz, CDCl$_3$): δ 0.91 (t, 3H); 1.51 (m, 2H); 2.14 (s, 3H); 2.2 (t, 2H); 5.9 (d, 1H); 10.0 (d, 1H). $^{13}$C NMR (67.5 MHz, CDCl$_3$): δ 14.01; 17.81; 20.69; 42.96; 127.75; 164.49; 191.67.

Preparation of Pyrone 5

To a flame-dried flask under a fluching argon atmosphere containing carboxylic acid 4a (10.55 gm, 91 mmol, 1 equiv dissolved in 250 mL of freshly distilled THF) was added carbonyldiimidazole (16.22 gm, 100 mmol, 1.1 equiv). The reaction was left stirring for 12 h before being concentrated via a rotary evaporator. The residue was partitioned between 100 mL of CHCl$_3$ and 100 mL of 10% HCl. The aqueous layer was extracted with CHCl$_3$ (2×50 mL). The combined organic layers were dried with Na$_2$SO$_4$, filtered and evaporated on a rotary evaporator. The product needed no further purification as long as it was left on a vacuum pump for sufficient duration in order to remove any remaining starting acid. This yielded compound 5 (8.8 gm, 98%) as a tan solid. $^1$H NMR (300 MHz, CDCl$_3$): δ 5.91 (s, 1H); 3.10 (q, J=7.3 Hz, 2H); 2.53 (q, J=7.2 Hz, 2H); 1.24 (t, J=7.5 Hz, 3H); 1.15 (t, J=7.2 Hz, 3H). $^{13}$C NMR (75 MHz, CDCl$_3$): δ 208.36; 181.16; 173.52; 161.16; 99.92; 99.56; 35.372; 27.52; 10.49; 7.78. MS (EI): calc. 196.0, anal. 196.0. IR (Film, KBr): $v_{max}$=3400 m (b), 3020 s, 1710 s (b), 1625 m (b), 1555 s (b), 1430 w (b), 1315 vs, 760 vs (b).

Preparation Iodide 8b

To a solution of imidazole (10.2 gm, 150 mmol) and triphenylphosphine (14.4 gm, 55 mmol) in CH$_2$Cl$_2$ (200 mL) at 0° C. was added I$_2$ (14.0 gm, 55 mmol). After 10 min, a solution of alcohol 8a (9.5 gm, 50 mmol) in CH$_2$Cl$_2$ (100 mL) was added over 5 min. The mixture was warmed to RT, covered in aluminum foil, and stirred for an additional 15 h in the dark. The reaction was then diluted with 2.0 mL saturated Na$_2$S$_2$O$_4$ aqueous solution before further dilution with water (150 mL). The organic layer was separated and the aqueous layer was back extracted with CH$_2$Cl$_2$ (2×80 mL). The combined organic layers were dried (MgSO$_4$), filtered, and concentrated in vacuo. The crude product was purified by flash chromatography (2% EtOAc in hexanes eluant) to afford iodide 8b (14.4 gm, 96% yield) as a pale oil. $^1$H NMR (400 MHz, CDCl$_3$): δ 3.64 (t, 2H); 3.25 (t, 2H); 1.96 (m, 2H); 0.87 (s, 9H); 0.05 (s, 6H). $^{13}$C NMR (67.5 MHz, CDCl$_3$): δ 62.32; 36.14; 25.90; 8.26; 3.61; −5.33.

Preparation of Allyl Alcohol 13a

To a white slurry solution of zirconocene dichloride (11.7 gm, 40 mmol) in 100 mL (CH$_2$)$_2$Cl$_2$ was added AlMe$_3$ (40 mL, 2.0 M in hexanes, 80 mmol) at 0° C., stirred for 45 min, and then warmed to RT for 1.5 h. To this lemon-yellow solution was added 1-pentyne (2.72 gm, 40 mmol, dissolved in 20 mL (CH$_2$)$_2$Cl$_2$) at RT. The reaction was allowed to stir for 3.0 h. Then the solvent and the unreacted trimethylalane were evaporated under reduced pressure (maximum 50° C., 0.3 mm Hg, 2~3 h). The remaining orange-yellow organic residue was extracted with dry hexanes (4×30 mL), and the yellow extract was transferred to a 500 mL round-bottom flask via a cannula. To this was added "BuLi (16 mL, 2.5 M in hexanes, 40 mmol) at 0° C. This orange-yellow slurry solution was stirred from 0° C. to RT for 1.5 h, and then THF (70 mL) was added to dissolve the precipitate. The resulting solution (homogeneous, brown-yellow color) was cannulated to a suspension of paraformaldehyde in THF under a N$_2$ atmosphere. This orange-yellow suspension solution was allowed to stir at RT for 20 min.

The reaction was cooled to 0° C. (ice water bath), ice was added to quench the reaction, and then saturated NH$_4$Cl (100 mL) was added. The ice bath was removed and the reaction was further acidified with 3 M HCl until the reaction turned to a clear yellow (homogeneous) solution. At this time, the reaction pH was 2~3. The organic layer was separated, and the aqueous layer was extracted with ether (2×150 mL). The organic extracts were combined and washed with a saturated solution NaHCO$_3$ (200 mL), then dried with Na$_2$SO$_4$, filtered and concentrated under reduced pressure to provide crude allylic alcohol 13a. The crude product was purified by flash chromatography (20% EtOAc in hexanes eluant) to afford alcohol 13a (3.37 gm, 74% yield) as a colorless oil. $^1$H NMR (400 MHz, CDCl$_3$): δ 5.4 (t, 1H); 4.1 (d, 2H); 1.9 (t, 2H); 1.65 (s, 3H); 1.4 (m, 2H); 0.85 (t, 3H). $^{13}$C NMR (75 MHz, CDCl$_3$): δ 139.15; 123.33; 59.01; 58.97; 41.54; 41.50; 20.61; 15.88; 13.57.

Preparation of Acid 4a

Ethyl propionate (25 gm, 175 mmol) was dissolved in 30 mL of 1.5 M solution NaOH and stirred at RT for 38 h. The reaction was cooled to 0° C., and 3 M HCl was slowly added until the reaction system reached a pH ~1, then solid KCl was added to saturate the reaction, followed by EtOAc extraction (3×100 mL), and CHCl$_3$ (2×100 mL). The combined organic layers were dried with Na$_2$SO$_4$, filtered and evaporated on a rotary evaporator. This protocol afforded the carboxylic acid 4a (15.5 gm, 76% yield) as a white solid. The product needed no further purification and was used directly in the next step. $^1$H NMR (300 MHz, CDCl$_3$): δ 3.52 (s, 2H); 2.60 (q, J=7.3 Hz, 2H); 1.10 (t, J=7.3 Hz, 3H). $^{13}$C NMR (75 MHz, CDCl$_3$): δ 204.28; 172.32; 47.87; 36.60; 7.45. MS (EI): calc. 116.1, anal. 116.1. IR (Film, KBr): $v_{max}$=3400 m (b), 3020 s, 1708 s (b), 1620 w, 1410 m, 1300 m, 1218 vs, 1110 w, 1040 w, 925 w, 760 vs.

Preparation of Alcohol 8a

To a suspension of NaH (4.0 gm, 100 mmol, 60% dispension in mineral oil) in THF (100 mL) at RT was added 1,3-propane diol (7.6 gm, 100 mmol, dissolved in 50 mL of THF) via a cannula. The resulting mixture was stirred at RT for 45 min, then a solution of TBSCl (15.0 gm, 100 mmol) in 50 mL THF was added into the reaction mixture by a cannula. This resulting reaction mixture was stirred for 1.0 h at RT. The reaction was quenched with saturated NaHCO$_3$ aqueous solution (200 mL), and extracted with ether (2×200 mL). The combined organic layers were dried (MgSO$_4$), filtered, and concentrated in vacuo. The crude product was purified by flash chromatography (20% EtOAc in petroleum ether eluant) to afford the pure mono-protected alcohol 8a (18.1 gm, 98% yield) as a clear oil. $^1$H NMR (400 MHz, CDCl$_3$): δ 3.73–3.80 (m, 4H); 2.71 (br s, 1H); 1.74 (m, 2H); 0.86 (s, 9H); 0.04 (s, 6H). $^{13}$C NMR (75 MHz, CDCl$_3$): δ 62.70; 62.16; 34.22; 25.89; 25.81; 25.76; 18.13; –5.55.

Preparation of Pyrone 5a

To a stirred solution of diisopropylamine (3.34 mL, 24 mmol) in 25 mL THF at –78° C. under an argon atmosphere was added n-butyl lithium (9.45 mL, 2.5 M solution in hexanes, 23.6 mmol). The mixture was allowed to warm to 0° C. for 30 min and then recooled to –78° C. The resulting solution was treated with a solution of pyrone 5 (1.47 gm, 7.5 mmol) in 10 mL of THF, and stirred for 1.0 h at –78° C. The derived dianion was treated with iodide 8b (2.5 gm, 8.25 mmol) in 10 mL THF, followed by the addition of HMPA (4.0 mL, 23.2 mmol). The reaction mixture was allowed to stir for 30 min at –78° C., before being diluted with saturated NH$_4$Cl aqueous solution (50 mL). The organic layer was separated, and the aqueous layer was extracted with ether (2×50 mL). All organic layers were combined and dried (MgSO$_4$), filtered, and concentrated in vacuo. The resulting crude oil was purified by flash chromatography (20% EtOAc in hexanes eluant) to afford the pure alkylation product 5a (2.4 gm, 87% yield) as a yellow oil. $^1$H NMR (400 MHz, CDCl$_3$): δ 5.90 (s, 1H); 3.57 (t, 2H); 3.08 (q, 2H); 2.56 (m, 1H); 1.43–1.73 (m, 3H); 1.22 (d, J=7.3 Hz, 3H); 1.13 (t, 3H); 0.86 (s, 9H); 0.01 (s, 6H). $^{13}$C NMR (67.5 MHz, CDCl$_3$): δ 207.81; 180.57; 175.56; 160.64; 99.28; 62.16; 38.27; 34.81; 29.99; 29.72; 25.44; 17.82; 17.48; 7.27; –5.82.

Preparation of Diol 5b

A solution of TBS ether 5a (1.66 gm, 4.5 mmol) in 50 mL of AcOH, THF, and water (3:1:1) was stirred at RT for 15 h. The reaction was diluted with 50 mL water, extracted with CHCl$_3$ (2×100 mL). The combined organic layers were washed with a NaHCO$_3$ saturated solution (1×200 mL). The organic layer was separated, and the aqueous layer was back extracted with CHCl$_3$ (1×100 mL). All combined organic layers were dried (MgSO$_4$), filtered, and concentrated in vacuo. The crude product was purified by flash chromatography (40% EtOAc in hexanes eluant) to afford diol 5b (1.04 gm, 91% yield) as a yellow oil. $^1$H NMR (400 MHz, CDCl$_3$): δ 5.90 (s, 1H); 3.63 (br s, 1H); 3.08 (q, 2H); 2.58 (m, 1H); 1.71–1.80 (m, 1H); 1.50–1.62 (m, 3H); 1.33 (br s, 1H); 1.23 (d, J=7.33 Hz, 3H); 1.13 (t, 3H). $^{13}$C NMR (67.5 MHz, CDCl$_3$): δ 180.45; 175.20; 160.62; 99.30; 99.03; 61.62; 38.14; 34.71; 29.83; 29.46; 17.32; 7.14; 1.51.

Preparation of Aldehyde 5c

To a solution of alcohol 5b (483 mg, 1.9 mmol) in CH$_2$Cl$_2$ (20 mL) was added pyridine (845 µL, 10.45 mmol), followed with Dess-Martin periodinate reagent (2.8 mg, 6.65 mmol) in one portion. The resulting reaction mixture was stirred at RT for 2.0 h before being quenched with saturated NaHCO$_3$ aqueous solution. The reaction mixture was extracted with CH$_2$Cl$_2$ (2×60 mL), dried (MgSO$_4$), filtered, and concentrated in vacuo. The crude product was flash chromatographed (15% EtOAc in hexanes eluant) to afford aldehyde 5c (417 mg, 87% yield) as yellow oil. $^1$H NMR (400 MHz, CDCl$_3$): δ 5.90 (s, 1H); 3.07 (q, 2H); 2.59 (m, 1H); 2.46 (t, 2H); 1.83–2.02 (m, 2H); 1.23 (d, J=7.33 Hz, 3H); 1.12 (t, 3H). $^{13}$C NMR (67.5 MHz, CDCl$_3$): δ 200.73; 180.69; 174.35; 160.62; 99.93; 99.45; 40.82; 37.82; 35.00; 25.87; 17.52; 7.43; 1.81.

Preparation of Acyl Pyrone Ester 15

To a solution of triethyl phosphonoacetate (1.4 gm, 6.24 mmol) in C$_6$H$_6$ (20 mL) at room temperature was added NaH (210 mg, 5.2 mmol, 60% dispension in mineral oil). The resulting reaction was stirred at RT for 15 min, before aldehyde 5c (525 mg, 2.08 mmol) in 15 mL C$_6$H$_6$ was added, via cannula. The reaction was allowed to stir at RT for 1.0 h before being diluted with aqueous NH$_4$Cl solution (50 mL). The mixture was extracted with EtOAc (2×100 mL), dried (MgSO$_4$), filtered, and concentrated in vacuo. The crude product was flash chromatographed (15% EtOAc in hexanes eluant) to afford compound 15 (596 mg, 89% yield) as a yellow oil. $^1$H NMR (400 MHz, CDCl$_3$): δ 6.89 (dt, J=6.8, 15.6 Hz, 1H); 5.93 (s, 1H); 5.82 (d, J=15.6 Hz, 1H); 4.17 (q, J=7.1 Hz, 2H); 3.11 (q, J=7.1 Hz, 2H); 2.60 (m, 1H); 2.21 (ddd, J=7.2, 7.3, 7.4 Hz, 2H); 1.89 (m, 1H); 1.69 (m, 1H); 1.28 (t, J=7.1 Hz, 3H); 1.25 (d, J=6.9 Hz, 3H); 1.16 (t, J=7.1 Hz, 3H). $^{13}$C NMR (75 MHz, CDCl$_3$): δ 208.38; 180.98; 174.93; 166.37; 161.00; 147.16; 122.38; 100.17; 99.78; 60.37; 38.36; 35.40; 32.32; 29.59; 17.86; 14.29; 7.77. IR (film, KBr): ν$_{max}$=2978 s, 2942 s, 1731 s (b), 1637 s, 1631 s, 1554 s, 1443 s, 1272 m, 1178 m, 1043 m.

Preparation of Pyrone Diol 14a

Compound 15 (55 mg, 0.17 mmol) was dissolved in 3.5 mL CH$_2$Cl$_2$ and stirred at –78° C. under argon atmosphere. To this yellow homogeneous solution was added freshly distilled TiCl$_4$ (75 µl, 0.68 mmol), the reaction turned to an orange-yellow slurry mixture instantly. After stirring for 30 min at –78° C., Et$_3$N (104 µL, 0.75 mmol) was added, and the reaction became a red-dark reaction mixture. This reaction mixture was allowed to stir at –78° C. for 3.0 h, then aldehyde 14 (57 mg, 0.51 mmol) dissolved in 2.0 mL CH$_2$Cl$_2$ was added via a cannula. This red-dark reaction mixture was stirred at –78° C. for 17 h before it was quenched with distilled water. The reaction was extracted with CHCl$_3$ (3×30 mL), dried (Na$_2$SO$_4$), and concentrated in vacuo. The crude product was flash chromatographed (25% EtOAc in hexanes eluant) to provide diol 14a (53 mg, 71% yield) as a sticky yellow oil. $^1$H NMR (400 MHz, CDCl$_3$): δ 6.86 (dt, 1H); 5.90 (s, 1H); 5.80 (d, J=15.87 Hz, 1H); 5.21 (d, J=8.55 Hz, 1H); 4.74 (m, 1H); 4.08–1.18 (m, 3H); 2.57 (m, 1H); 2.42 (br s, 1H); 2.19 (dt, 2H); 1.94 (t, 2H); 1.83–1.90 (m, 1H); 1.65 (s, 3H); 1.60–1.70 (m, 1H); 1.30–1.43 (m, 2H); 1.19–1.27 (m, 9H); 0.82 (t, 3H).

Preparation of Pyrone Ester 17

A stirred solution of diol 14a (52 mg, 0.12 mmol) in 4 mL CH$_2$Cl$_2$ was cooled to –15° C. To this solution was added Et$_3$N (67 µL, 0.48 mmol), followed by MsCl (28 µL, 0.36 mmol). The yellow solution was stirred at –15° C. for 30 min, and then warmed to 0° C. for 15 h. To this was added DBU (108 µL, 0.72 mmol), the resulting reaction mixture was stirred from 0° C. to RT over a 12 h time period before being diluted with 2% HCl aqueous solution (10 mL). The mixture was stirred for 5 min then extracted with EtOAc (2×15 mL), dried (Na$_2$SO$_4$), filtered and concentrated in vacuo. The crude product was flash chromatographed (20% EtOAc in hexanes eluant) to provide compound 17 (36 mg, 72% yield) as yellow oil. $^1$H NMR (400 MHz, CDCl$_3$): δ 7.00 (d, J=11.6 Hz, 1H); 6.91 (dt, J=6.8, 15.6 Hz, 1H); 6.16 (d, J=11.6 Hz, 1H); 5.95 (s, 1H); 5.83 (d, J=15.6 Hz, 1H); 4.19 (q, J=7.1 Hz, 2H); 2.61 (m, 1H); 2.24 (m, 2H); 2.15 (t, J=7.6 Hz, 2H); 1.91 (m, 1H); 2.01 (s, 3H); 1.85 (s, 3H); 1.69 (m, 1H); 1.49 (m, 2H); 1.29 (t, J=7.1 Hz, 3 H); 1.27 (d, J=6.9 Hz, 3H); 0.91 (t, J=7.3 Hz, 3H). $^{13}$C NMR (75 MHz, CDCl$_3$): δ 201.72; 180.83; 174.82; 166.42; 160.39; 149.17; 147.25; 133.65; 133.04; 122.37; 120.67; 100.06; 99.17; 60.38; 42.93; 38.27; 32.25; 29.62; 21.04; 17.81; 17.30;

14.29; 13.88; 13.55. MS (FABMS): (M+H) calc. 417, anal. 417. IR (Film, KBr): $v_{max}$=2966 m, 2931 m, 2872 m, 1748 s, 1736 s, 1719 s, 1701 s, 1560 s, 1542 s, 1454 s.

Discussion

Figure 2:
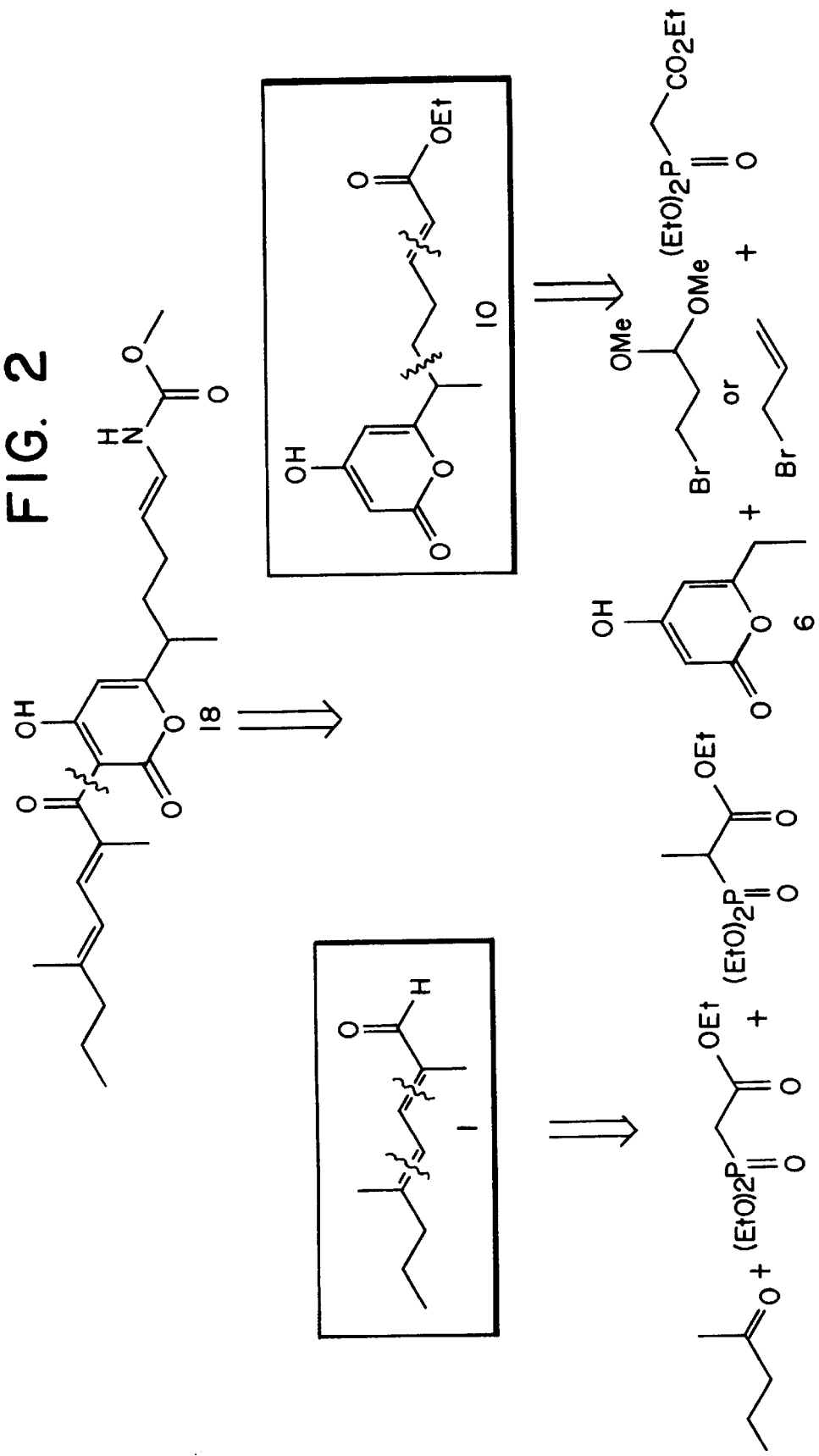
FIG. 2 illustrates a retrosynthetic analysis for the preparation of myxopyronin A.

The total synthesis of myxopyronin A was approached in several ways. The first is shown in the retrosynthesis provided in FIG. 2.

Figure 3:
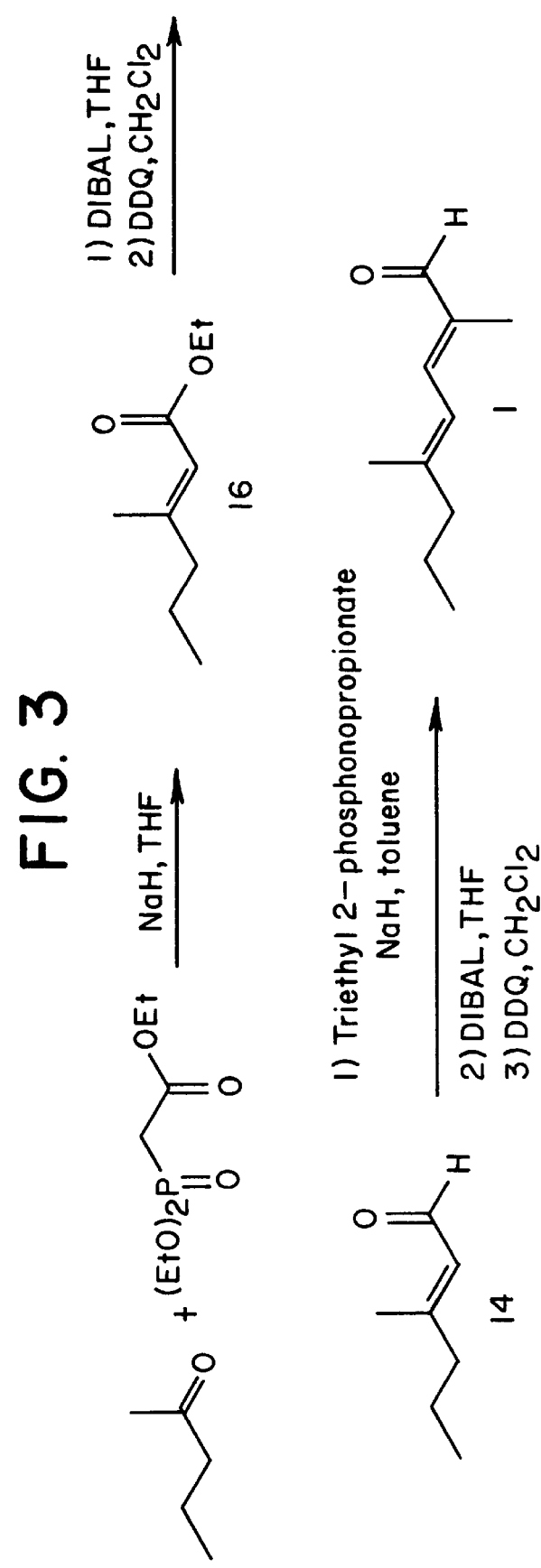
FIG. 3 illustrates the synthesis of compound 1 in accord with the present invention.

Attachment of the 3-position side chain was accomplished through an aldol condensation. Ester 1 is available from 2-pentanone through Wadsworth-Emmons chemistry (Wadsworth, W., Emmons, W., *Org. Synth.*, 1965, 45, 44) and commercially available triethylphosphonates (FIG. 3). The anion of triethyl phosphonacetate is created by stirring with NaH in THF, and is condensed with 2-pentanone to create unsaturated ester 16. The ester 16 is reduced with DIBAL to the alcohol and then oxidized to the aldehyde 14 with DDQ. Compound 1 is produced by going through another cycle of Wadsworth-Emmons chemistry, DIBAL reduction and DDQ oxidation. Intermediate 13 can also be made using lithium dimethyl cuprate chemistry (Sum and Weiler, *Can. J. Chem.*, 1979, 57, 1431), which procedure produces 13 in a higher E/Z ratio.

The other half of the molecule containing the 6-substituted pyrone is dissected in the following manner. This scheme requires a pyrone functionalized at the 6-position (Douglas, J., Money, T., *Can. J. Chem.*, 1968, 46, 695) and commercially available reagents shown in FIG. 2. The three necessary segments can be joined by an additional Wadsworth-Emmons olefination and a simple alkylation. The terminal methyl carbamate can then be introduced by the use of a modified Curtius rearrangement. Overman, L., Taylor, G., Petty, C., Jessup, P., *J. Org. Chem.*, 1978, 43, 2164.

Figure 4:
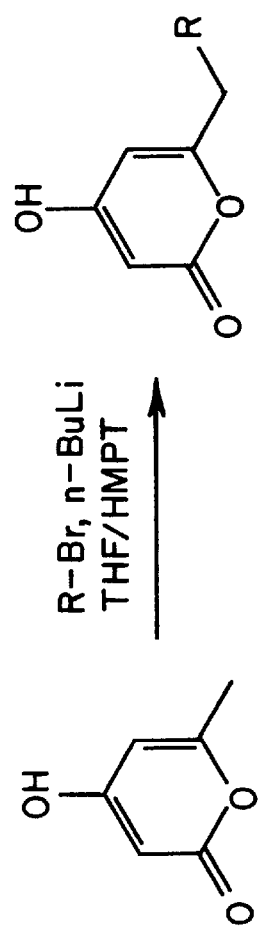
FIG. 4 illustrates alkylation of the 7-position of compound 3 for the preparation of compound 10.
Figure 5:
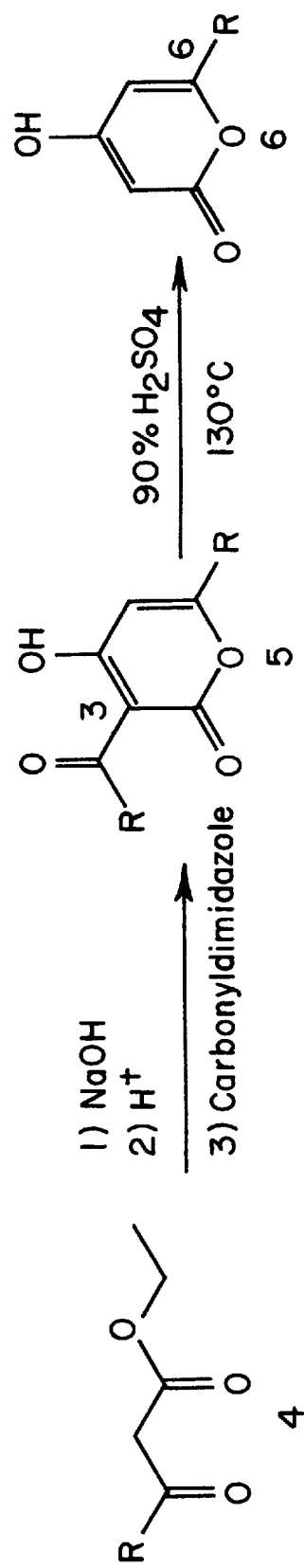
FIG. 5 illustrates the synthesis of compound 6 in accord with the present invention.

Two different pathways are provided for the synthesis of compound 10. The first pathway is based on the known alkylation of the commercially available compound 3 at the 7-postion using n-BuLi and an alkyl halide. Groutas, W., Stanga, M., Brubaker, M., Huang, T., Moi, M., Carroll, R., *J. Med. Chem.*, 1985, 28, 1106. (see FIG. 4) A model pyrone containing an ethyl group was alkylated at the 7-position in a similar manner by constructing the 6-position side chain after the desired methyl group (C-8) was already in place at C-7. (The synthetic approach used to synthesize the 6-ethyl pyrone was developed by Cook and co-workers. Cook, L., Ternai, B., Ghosh, P., *J. Med. Chem.*, 1987, 30, 1017.) The present invention provides a means of installing alkyl chains of varying sizes at the 6-position by dimerization of various ethyl malonates and subsequent deacylation of the 3-position (FIGS. 5 and 15). Thereby, pyrone 6 is prepared where R is ethyl.

Pyrone 6 is then alkylated with 3-bromopropionaldehyde dimethyl acetal and the 4-hydroxyl group protected as its SEM ether (FIG. 6). The dimethyl acetal is removed with dilute $H_2SO_4$. The Wadsworth-Emmons reaction (Wadsworth, W., Emmons, W., *Org. Synth.*, 1965,45,44) introduces the unsaturated ester, and the SEM group is removed with TBAF to produce key intermediate 10. The 3-position side chain is introduced by use of an aldol reaction. The ester on the 6-position side chain is hydrolyzed, and a Curtius rearrangement installs a vinyl carbamate moiety to complete the synthesis of myxopyronin A.

In a preferred embodiment, the present invention provides an improved route to intermediate 10. Allyl bromide alkylates pyrone 6 in a higher yield (FIG. 7). This modification combined with the use of dilute $H_2SO_4$ in place of TBAF to remove the SEM group substantially increases the overall yield of 10.

FIG. 8 schematically demonstrates the completion of the myxopyronin A synthesis from key intermediate 10. Aldol condensation with 1 to produce 13 is followed by oxidation with any reagent effective for oxidizing alcohols at allylic or benzylic positions, including DDQ, MnO2, $K_2CrO_7$, etc., to afford ketone 17. Conversion of the ethyl ester to the acid is effected by saponification with LiOH. Finally, installation of the vinyl carbamate is effected by modified Curtius conditions.

In addition, the present invention provides an alternate pathway for the total synthesis of myxopyronin A. Formation of the bond between C-3 and C-15 has proven to be a difficult synthetic step. A study of alternative ways of appending the 3-position side chain demonstrated that attachment of a portion of the 3-position alkyl chain is effectively performed by acylation of the pyrone. This process is based on acylation of 6-alkyl-4-hydroxy-2-pyrones by acyl chlorides. Cook, L., Ternai, B., Ghosh, P., *J. Med. Chem.*, 1987, 30, 1017. However, acylation of pyrone 10 with acyl chloride 19 using conditions set forth by Cook (FIG. 9) did not provide the expected product: no evidence of the double bonds were observed by NMR; only compound 10 was recovered.

Acylation of pyrones is successful when acid chlorides with saturated alkyl chains are used. A retrosynthetic analysis of the preparation of myxopyronin A taking advantage of this reaction is shown, in FIG. 10. Pyrone 10 was synthesized as shown in FIGS. 5–7. At this point, the pyrone is acylated with propionyl chloride. The rest of the 6-position side chain is then attached using a base-catalyzed aldol reaction with aldehyde 14, an intermediate in the synthesis of 1 (FIG. 3) and the 3-propionyl pyrone 15. The synthesis is completed with a Curtius rearrangement as illustrated in FIG. 8.

The alternate route works effectively as disclosed herein. Pyrone intermediate 10 is acylated with propionyl chloride in TFA to give compound 15. An aldol reaction using LDA in THF condenses aldehyde 14 with 15. Subsequent treatment with MsCl and DBU gives the desired diene in the side chain and yields intermediate 17.

Analogs of Myxopyronins

As will be apparent to one of skill in the art, various isomers (including stereoisomers), analogs, and derivatives of the pyronins are made accessible by the subject invention by appropriate modification. For example, the total synthesis of myxopyronin B is easily carried out by simply substituting 2-hexanone for 2-pentanone at the beginning of the synthesis (FIG. 3). As disclosed herein, the synthetic pathways provide a mixture of enantiomers which can be prepared in purified form by any of a variety of methods well known in the art, including but not limited to chiral HPLC, resolution of one of the intermediates set forth herein, or separation of a diastereomeric derivative.

Convergent Synthesis of Myxopyronin A

Figure 1A:
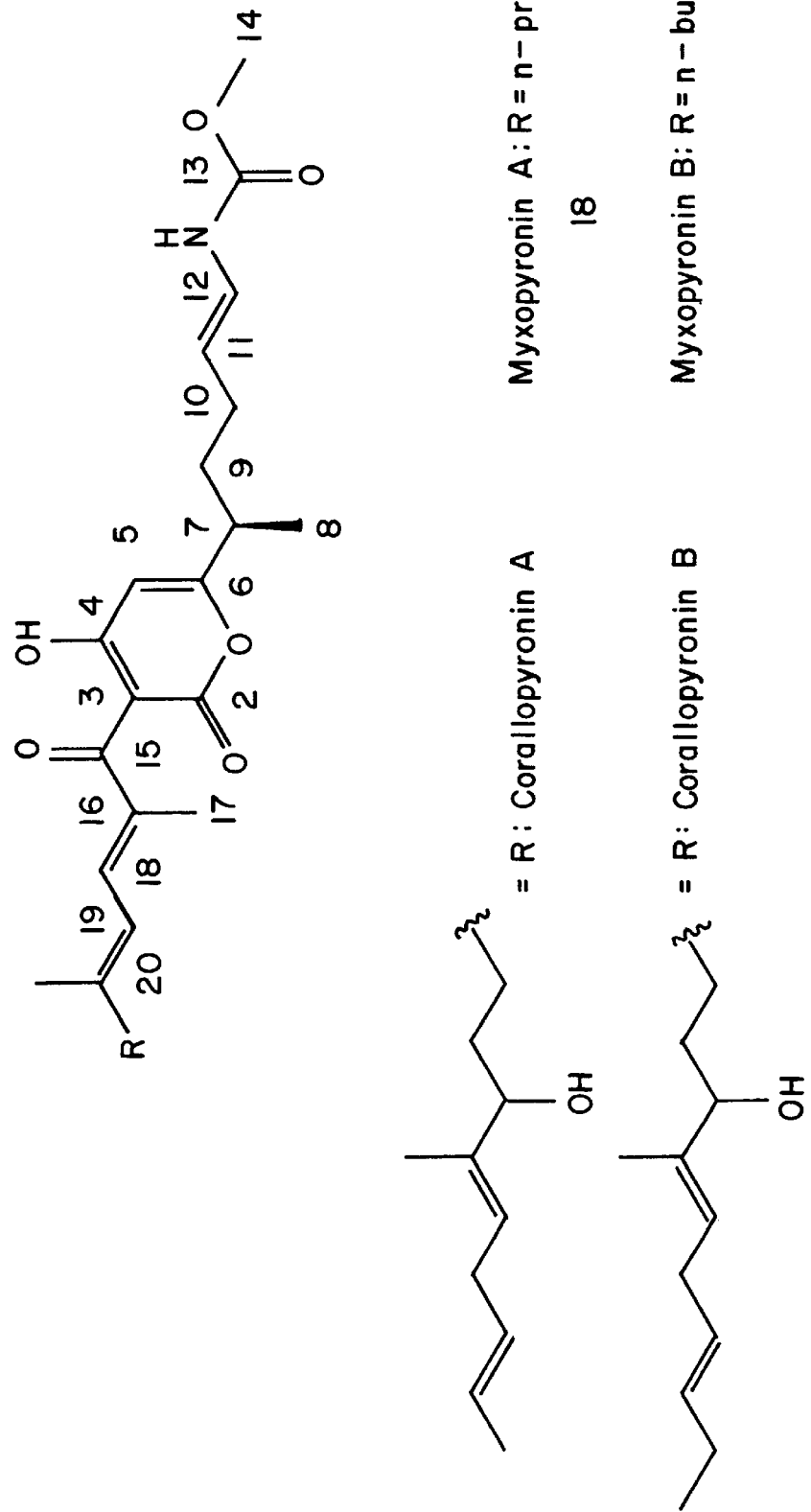
FIG. 1(*a*) shows the structures of corallopyronin A/B and myxopyronin A/B.
Figure 1B:
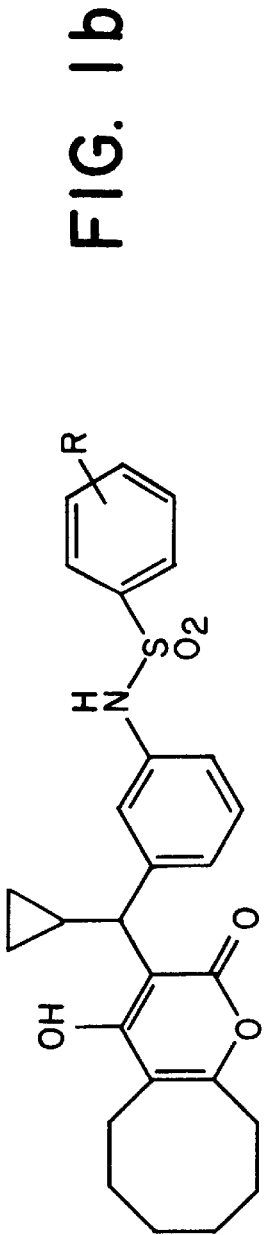

Pyrones have been used to elicit a biological effect in a few instances but in none of them have they been used as an antibacterial agent. 2H-pyran-2,6(3H)-dione derivatives are reported to be active at reasonable doses in a passive cutaneous anaphylaxis model in rats when administered by either the intravenous or oral route. Snader, K. M. et al., *J. Med. Chem.*, 1979, 22, 706; Chahrin, L. W., Snader, K. M., Williams, C. R., 2H-Pyran-2,6(3H)-dionederivate, German Patent 25 33 843. In a second case, simple 3-(1-oxoalkyl)-4-hydroxy-6-alkyl-2-pyrones were found to be effective in vitro in the inhibition of human sputum elastase. Cook, L., Ternai, B., Ghosh, P., *J . Med. Chem.*, 1987, 30, 1017. Lastly, a series of coumarin derivatives were found to be effective inhibitors of HIV protease in both enzymatic assays and cell culture (FIG. 1(b)). Skulnick, H. I., et al., *J. Med. Chem.*, 1995, 38, 4968. No synthetic investigations of pyronin antibacterials have been reported in the literature. The total synthesis of myxopyronin A was approached in a highly convergent manner. The retrosynthesis of myxopyronin A is shown in FIG. 11.

Preparation of compound 14 (FIG. 12(a)) was started from commercially available 1-pentyne. Regioselective and ster-eospecific carboalumination of 1-pentyne in the presence of 2.0 equiv of AlMe$_3$ and 1.0 equiv of Cp$_2$ZrCl$_2$ (Cp=η-C$_5$H$_5$) afforded the organoalane species, which was treated with 1.0 equiv of $^n$-BuLi, and quenched with paraformaldehyde to give geometrically pure (E) allylic alcohol 13a with 74% yield. Swern oxidation of alcohol 13a cleanly generated versatile aldehyde 14, which is not very stable and used immediately after flash chromatography.

A synthetic approach to pyrone 5 (R=Et) (FIG. 12(b)) was based on a known procedure reported by Cook and co-workers (supra). Commercially available ethyl propionylacetate was hydrolyzed under basic conditions (1.5 M aqueous NaOH) to provide acid 4a (76% yield), which was dimerized, in the presence of carbonyldiimidazole, to afford pyrone 5 (R=Et) in 98% yield. This sequence of reactions easily provided a quantitative amount of pyrone 5 (R=Et), which is the core structure in the myxopyronin A structure.

Preparation of compound 8b (FIG. 12(c)) is straight forward. Monoprotection of 1,3-propane diol was achieved by using 1.0 equiv of NaH and 1.0 equiv of TBSCl, and it cleanly generated alcohol 8a in 98% isolated yield. Iodination of alcohol 8a under the condition of I$_2$/PPh$_3$/imidazole provided iodide 8b as a single product with 96% yield.

Subsequent research has led to an improved synthetic approach to the intermediate 15 (FIG. 13(a)). Pyrone 5 (R=Et) was lithiated (3.2 equiv of LDA) at −78° C., the derived anion was treated with iodide 8b to afford compound 5a as a single alkylated product in 80–87% isolated yield. Compound 5a was deprotonated (AcOH/THF/H$_2$O, 2:2:1 mixture solution) at RT to provide alcohol 5b (91% yield), which was oxidized in the presence of the Dess-Martin periodinate reagent to yield aldehyde 5c. Wadsworth-Emmons homologation of aldehyde 5c (triethyl phosphonoacetate, NaH, C$_6$H$_6$) cleanly generated α,β-unsaturated ester 15 as a single isomer with a 89% yield. FIG. 13(b) schematically demonstrates the completion of the myxopyronin A synthesis from key intermediate 15.

Aldol condensation of ethyl ketone 15 with aldehyde 14 in the presence of TiCl$_4$ was investigated. Titanium enolate was generated at −78° C. by the treatment of ethyl ketone 15 with 4.0 equiv of TiCl$_4$ and 4.4 equiv of Et$_3$N. The derived (Z)-enolate was condensed with an excess of freshly prepared aldehyde 14 to produce diol 14a in 71.3% isolated yield. Treatment of diol 14a with methane sulfonyl chloride, followed by elimination mediated by DBU, furnished the trisubstituted diene 17 in a 72% yield. Conversion of 17 to the α,β-unsaturated acid 17a was accomplished with LiOH. Finally, installation of the vinyl carbamate functional group was effected through modified Curtius condition. Acid 17a was combined with diphenylphosphoryl azide (PhO$_2$P(O)N$_3$) and Et$_3$N and refluxed in C$_6$H$_6$ for 9.0 h. The derived azide intermediate was treated with anhydrous MeOH and was refluxed for another 6.0 h to produce (±)myxopyronin A, compound 18.

Myxopyronin A Synthesis Aldolization of an Acyl Pyrone

Acylation of pyrones at the 3-position is successful when the acid chlorides of short, saturated alkyl chains are used. Douglas, J., Money, T., *Can. J. Chem.*, 1968, 46, 695.

Acylation of 10 with propionyl chloride is followed by a base-catalyzed aldol with the appropriate aldehyde to attach the rest of the native side-chain. The necessary aldehyde 14 (FIG. 14(a)) is generated by way of the ester 16. (Sum, F. W., Weiler, L., *Can. J. Chem.*, 1979, 57, 431) Reaction of ethyl butyrylacetate with diethyl chlorophosphite and LiMe$_2$Cu gave predominantly the E, isomer of 16 after distillation. DIBAL reduction to the alcohol followed by Swern oxidation produced the aldehyde 14.

With aldehyde 14 in hand, the route shown in FIG. 14(b) was used to complete the synthesis of myxopyronin A. Pyrone intermediate 10 is acylated with propionyl chloride in TFA to give compound 15. The overall conversion is efficient since unreacted starting material can be recovered by chromatography. An aldol reaction between the pure regioisomer of 14 and 15 was performed using LDA in THF. The crude alcohol was converted to the mesylate and then eliminated using DBU. This yielded the desired diene 17.

To complete the synthesis, 17 was saponified to the acid using LiOH. A modified Curtius sequence (Overman, L., Taylor, G., Petty, C., Jessup, P., *J. Org. Chem.*, 1978, 43, 2164) was then used to install the unusual vinyl carbamate moiety and thereby afford the desired myxopyronin A. The identity of the product was confirmed by comparison of spectral data for the synthetic product with that of an authentic sample of the natural product. Resolution of the enantiomers generated at C-7 may be achieved by means of chiral HPLC.

What is claimed is:

1. A process of preparing a myxopyronin having the structure:

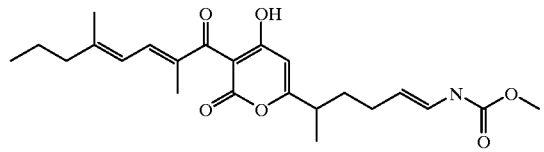

which comprises:

(a) reacting an acyl pyrone having the structure:

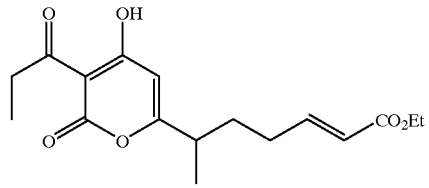

with an unsaturated aldehyde having the structure:

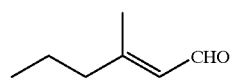

to form a pyrone aldol having the structure:

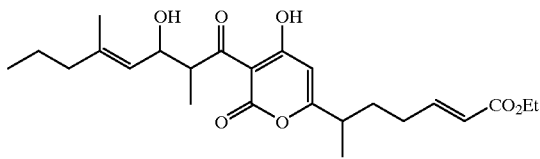

(b) (i) mesylating the pyrone aldol formed in step (a) to form a pyrone aldol mesylate; and
(ii) reacting the pyrone aldol mesylate formed in step (b) (i) to form a pyrone diene having the structure:

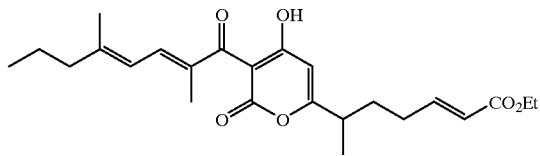

and
(c) saponifying the pyrone diene formed in step (b) (ii) to form a pyrone acid;
(d) converting the pyrone acid formed in step (c) to a pyrone acyl azide; and
(e) solvolyzing the pyrone acyl azide formed in step (d) with methanol to form the myxopyronin.

2. The process of claim 1 wherein the acyl pyrone in step (a) is treated with the unsaturated aldehyde in the presence of a Lewis acid catalyst.

3. The process of claim 2 wherein the Lewis acid catalyst is titanium tetrachloride/triethylamine combination.

4. The process of claim 1 wherein the pyrone aldol in step (b) (i) is mesylated with mesylchloride in the presence of triethylamine.

5. The process of claim 1 wherein the pyrene aldol mesylate in step (b) (ii) is reacted with 1,8-diazabicyclo [5.4.0] undec-7-ene.

6. The process of claim 1 wherein the pyrone diene in step (c) is saponified with lithium hydroxide.

7. The process of claim 1 wherein the pyrone acid in step (d) is converted using diphenylphosphoryl azide in the presence of triethylamine.

8. A compound having the structure

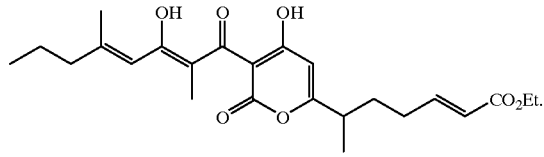

* * * * *